United States Patent
Wang et al.

(10) Patent No.: US 6,608,196 B2
(45) Date of Patent: Aug. 19, 2003

(54) PROCESS FOR SOLID SUPPORTED SYNTHESIS OF PYRUVATE-DERIVED COMPOUNDS

(75) Inventors: Bing Wang, Cupertino, CA (US); Satyanarayana Janagani, Santa Clara, CA (US); Wyeth B. Callaway, Austin, TX (US); Jonathan L. Sessler, Austin, TX (US)

(73) Assignee: Galileo Pharmaceuticals, Inc., Santa Clara, CA (US)

(*) Notice: Subject to any disclaimer, the term of this patent is extended or adjusted under 35 U.S.C. 154(b) by 0 days.

(21) Appl. No.: 10/138,032

(22) Filed: May 3, 2002

(65) Prior Publication Data

US 2003/0100750 A1 May 29, 2003

Related U.S. Application Data

(60) Provisional application No. 60/288,649, filed on May 3, 2001.

(51) Int. Cl.$^7$ .................. C07D 413/00; C07D 265/30; C07D 401/00; C07D 321/00; C07D 249/00
(52) U.S. Cl. ................... 544/130; 544/162; 544/171; 544/365; 544/399; 546/208; 546/226; 546/242; 546/246; 548/569; 560/17; 560/168; 562/440; 564/162; 564/163; 564/194
(58) Field of Search .................. 544/130, 162, 544/171, 365, 399; 546/226, 208, 242, 246; 548/569; 560/17, 168; 562/440; 564/162, 163, 194

(56) References Cited

U.S. PATENT DOCUMENTS

| | | | |
|---|---|---|---|
| 5,002,963 A | 3/1991 | De Luca et al. | |
| 5,047,427 A | 9/1991 | Williamson | |
| 5,075,210 A | 12/1991 | Wilkman-Coffelt | |
| 5,142,056 A | 8/1992 | Kempe et al. | |
| 5,210,215 A | 5/1993 | Politi et al. | |
| 5,256,697 A | 10/1993 | Miller et al. | |
| 5,294,641 A | 3/1994 | Stanko | |
| 5,395,822 A | 3/1995 | Izumi et al. | |
| 5,545,568 A | 8/1996 | Ellman | |
| 5,859,031 A | 1/1999 | Hamilton et al. | |
| 5,968,727 A | 10/1999 | Brunengraber et al. | |
| 6,057,312 A | 5/2000 | Cho et al. | |
| 6,086,789 A | 7/2000 | Brunengraber et al. | |
| 6,093,798 A | 7/2000 | Floyd et al. | |
| 6,127,190 A | 10/2000 | Lebl | |
| 6,221,637 B1 | 4/2001 | Hida et al. | |
| 6,331,537 B1 | 12/2001 | Hamilton et al. | |
| 6,392,010 B1 * | 5/2002 | Salvino et al. | 528/486 |

FOREIGN PATENT DOCUMENTS

| | | |
|---|---|---|
| EP | 288789 | 11/1988 |
| EP | 1065200 | 3/2001 |
| GB | 2076803 | 12/1981 |
| SU | 686308 | 10/1981 |
| WO | WO 99/43651 | 9/1999 |
| WO | WO 01/40206 | 6/2001 |

OTHER PUBLICATIONS

Yan, B. et al. (1998). "Quantitativel Monitoring of Solid–Phase Organic Synthesis by Combustion Elemental Analysis" *Tetrahedron*, 54, 11755–11766.

Hu, L. et al. (1990). "Inhibition of Cathepsin B and Papain by Peptidyl alpha–Keto Esters, alpha–Keto Amides, alpha–Diketones, and alpha–Keto Acids" *Archives of Biochemistry and Biophysics* 281(2):271–274.

Bonnema, J., et al. (1960). "Chemistry of Acetylenic Ethers XLIV" *Recueil*. 79:937–949.

Sokolov, M.P. et al. (1986). "Synthesis and Structure of Methyl 2–Oxo–3–Meslypropanoate" *Journal of Organic Chemistry of the USSR*. 22(4):644–647.

Bedeschi, A. et al. (1982). "Synthesis and *In Vitro* Activity of Some 7–[2–Metholyimino–(Substitiuted Thio)Alkanoyl] Amino Cephalosporanic Acid Derivatives" *Journal of Antibiotics*. 35(6):712–720.

Cavero, M. et al. (2001). "Studies on the intermolecular free radical addition of thionitrites to alkenes: a convenient method of the preparation of alpha–tritylthio oximes and related derivatives" *Tetrahedron Letters* 42:4377–4379.

Gilchrist, T.L. et al. (1987) "Reaction of Azoles with Ethyl Bromopyruvated Oxime: Alkylation by Substitution and by Elimination–Addition" *J. Chem. Soc. Perkin Trans.* 1(10):2235–2240.

Gilchrist, T. et al. (1979). "Ethyl 3–Bromo–2–hydroxyiminopropanoate, a Reagent for the Preparation of Ethyl Esters of alpha–Amino Acids" *Journal of the Chemical Society, Chem. Comm.* 1089–1090.

Sidky, M.M. et al. (1972) "Mannich Bases of Glyoxylanilide 2–Oximes and Their Effect on Photosyntetic Electron Transport" *Z. Naturforssch*. 27b:797–799.

Milyutin, A.V. et al. (1997) "Synthesis, properties and biological activity of 3–pyridylamides of 4–aryl–2–hydroxy–4–oxo–2–butenoic (aroylpyruvic) acids" *Khimiko–Farmatsevticheskii Zhurnal*. 31(1):32–35. (abstract).

Milytuin, A.V. et al. (1996). "Biologically active compounds in the series of aroylpyruvic acid beta–acetylamino– and beta–arylsulfonylaminoethylamides" *Khimiko–Farmatsevticheskii Zhurnal*. 30(6): 20–22. (abstract).

(List continued on next page.)

Primary Examiner—Richard L. Raymond
Assistant Examiner—Zachary C. Tucker
(74) Attorney, Agent, or Firm—Morrison & Foerster LLP

(57) ABSTRACT

Provided are processes for synthesizing structurally diverse pyruvate-derived compounds using a parallel approach on a solid phase support. Examples of such a solid phase support include resins which have also been used in solid phase peptide synthesis.

22 Claims, No Drawings

OTHER PUBLICATIONS

Igidov, N. et al. (1996). "Amides and hydrazides of acylpyruvic acids. 4. Synthesis and pharmacological activity of some amides of aroyl–and pivaloyl pyruvic acids" *Khimiko–Farmatsevticheskii Zhurna.l* 30(11):21–25. (abstract).

Milytuin, A. V. et al. (1996). "Synthesis of biological activity of aroylpyruvic acid pyridylamides" *Khimiko–Farmatsevticheskii Zhurnal.* 30(5):47–49. (abstract).

Yanborisov, T.N. et al. (1995). "Reaction of 5–aryl–2, 3–furandiones with 4–amino–3–R–4H–1,2,4–triazoles and antimicrobial activity of the reaction products" *Khimiko–Farmatsevticheskii Zhurnal.* 29(8):29–31. (abstract).

Nekrasov, D.D. et al. (1995). "Reaction of 5–aryl–2, 3–furandionies with aminoaryl thiocyanates" *Zh. Organic khim.* . 31(6):907–910. (abstract).

Demina, L.M. et al. (1992). "Synthesis, properties, and biological activity of 2–substituted 1–aryl–7–methyl (5,7–dimethyl)–4–oxy–1,4–dihydropyrido[2,3–d]pyrimidines" *Khimiko–Farmatsevticheskii Zhurnal.* 26(3):45–48. (abstract).

Andreichikov, Y.S. et al. (1989). "[(Aroylpyruvolyl)amino] benzonitriles and 3–phenacylidene–6(7)–cyano–3, 4–dihydro–2–quinoxalinones" *Khimiko–Farmatsevticheskii Zhurnal* 23(8):946–949. (abstract).

Andreichikov, Y.S. et al., (1977). "Chemistry of oxalyl derivatives of methyl ketones. XVII. Synthesis and biological activity of the esters of arlylsulfonylpyruvic acids and their derivatives" *Khimiko–Farmatsevticheskii Zhurnal* 11(10):85–89. (abstract).

Andreichikov, Y.S. et al. (1997). "Chemistry of oxalyl derivatives of methyl ketones. VIII. Synthesis and properties of arylsulfonylpyroracemic acid esters" *Zh. Organic Khim.* 13(10):2070–2074. (abstract).

Ohta, M. et al. (1968). "Ring closure of N–substituted N–acetylglycines with acid chlorides" *Nippon Kaguku Zasshi* 89(7): 714–716. (abstract).

* cited by examiner

PROCESS FOR SOLID SUPPORTED SYNTHESIS OF PYRUVATE-DERIVED COMPOUNDS

CROSS-REFERENCE TO RELATED APPLICATIONS

This application claims the benefit of U.S. Provisional Application Ser. No. 60/288,649, filed May 3, 2001, the disclosure of which is incorporated herein by reference in its entirety.

TECHNICAL FIELD

This invention primarily relates to a method for synthesis of structurally diverse pyruvate-derived compounds using a parallel approach on a solid phase support.

BACKGROUND ART

Pyruvate is a three-carbon (triose) ketoacid that is produced in biological systems in the end stages of glycolysis, a product of sugar metabolism. It is also a breakdown product of certain amino acids (alanine, glycine, cysteine, serine). Pyruvate can be reduced to lactate in the cytoplasm, a fermentative event in mammalian cells, or oxidatively decarboxylated to acetyl CoA in the mitochondrion.

Pyruvate itself, as well as certain pyruvate derivatives, have been promoted for use in treating disorders and promoting health. For example, pyruvate is sold as a dietary supplement for use in promoting weight loss and enhancing energy. It has also been suggested as a therapeutic intervention for clinical management of myocardial insufficiency (Mallet, R. T. (2000) "Pyruvate: metabolic protector of cardiac performance," *Proc. Soc. Exp. Biol. Med.* 223(2): 136–148) and the prevention of the adverse effects of myocardial ischemia. U.S. Pat. No. 5,294,641 discloses the use of pyruvate for treating a patient prior to or during heart trauma. U.S. Pat. No. 5,075,210 describes the use of pyruvate or pyruvate salts as a component in a cardioplegic solution and in preservation solutions for the heart before transplantation. U.S. Pat. No. 5,395,822 describes the use of certain pyruvate salts to protect against neuronal degeneration as a consequence of ischemia.

U.S. Pat. No. 6,086,789 describes certain pyruvate derivatives as useful for dermatologic indications as well as in treating diabetic ketosis, myocardial ischemia, injured organs and in lowering cholesterol and preventing acute hepatic effects of ethanol. Related U.S. Pat. No. 5,968,727 describes the use of pyruvate thioesters, such as cysteine, methionine and homocysteine, and glycerol pyruvate esters and dihydroxyacetone-pyruvate esters, in organ preservation solutions and for ischemia.

Similarly, pyruvate and pyruvyl amino acid conjugates have been suggested for use in diabetes (e.g., U.S. Pat. Nos. 5,047,427 and 5,256,697).

Heretofore, pyruvate derivatives and analogs have been synthesized using standard solution chemical methods. While such methods may be effective for a specific compound, they can be cumbersome when it is desirable to produce a large number of structurally similar compounds. The present invention provides a solid phase synthetic method that facilitates rapid synthesis and purification of a wide variety of pyruvate analogues, modified pyruvate analogues, and pyruvate-derived compounds, as defined below. In addition, the invention provides the basis for combinatorial approaches to producing and selecting pyruvate-derived compounds for use in any of a number of medical and cosmetic indications, including, but not limited to those described above. Using the methods provided, libraries of compounds can be formed and active compositions selected, using specified criteria and standard selection methods. All references disclosed herein are hereby incorporated in their entirety.

DISCLOSURE OF THE INVENTION

Methods for the solid phase synthesis of structurally diverse pyruvate-derived compounds are provided. These methods also encompass a parallel approach in which, after a given step the intermediates, tethered to the solid support, may be easily split and parallel synthetic pathways pursued to yield a number of different products. The methods described herein may be used to synthesize a variety of pyruvate-derived compounds, including, for example, but not limited to oximes, pyruvate analogues, modified pyruvate analogues, esters of pyruvate, including, but not limited to, polyol-pyruvate esters, pyruvate amides, pyruvate thioesters, glycerol-pyruvate esters, and dihydroxyacetone-pyruvate esters. These methods may be used with diverse classes of starting materials subsequently yielding a wide variety of functional groups. Such compounds have a wide variety of uses, both medical and as health supplements.

Accordingly, in a particular embodiment a method including a process for the synthesis of pyruvate-derived compounds, wherein the process comprises the steps, preferably but not necessarily, in order of a) forming an imine at the ketone position of an alpha-keto acid comprising β-leaving group with a solid-supported hydroxylamine to form a solid-supported intermediate;

b) esterifying the solid-supported intermediate formed in step a with a compound $R^1$—OH to form an $R^1$-substituted solid-supported intermediate;

c) performing a nucleophilic substitution of the $R^1$-substituted solid-supported intermediate obtained in step b with a compound $R^2X(H)$ to form an $R^2$-substituted solid-supported intermediate; and, optionally, d) cleaving the $R^2$-substituted solid-supported intermediate obtained in step c from the solid support to yield a pyruvate-derived compound.

Alpha-keto acids comprising a β-leaving group, preferably a pyruvic acid containing a β-leaving group such as a halogen, may be used to practice the present invention. Leaving groups are well known in the art. Examples of such compounds include 3-bromopyruvic acid, commonly known as bromopyruvic acid, and commercially available from Aldrich (Milwaukee, Wis.). Other examples of substituted pyruvic acids of use in the methods presented herein include chloropyruvic acid and iodopyruvic acid. Other examples of good leaving groups include, but are not limited to, mesylate and tosylate.

R-groups, including $R^1$—OH, $R^2X$— and $R^3$— of use in the methods of the present invention are described herein, as are exemplary $R^3$-containing acyl compounds. Additionally, examples of such are shown in Schemes A, B, C, D, E and F.

Further embodiments described herein may also include one or a combination of additional steps of, for example:

i) (a) reducing the $R^2$-substituted solid-supported intermediate to an amine to form an amine-substituted solid supported intermediate; and, (b) acylating the amine-substituted solid-supported intermediate with $R^3CO$— to form an $R^3$-substituted solid-supported intermediate;
wherein the above steps ia and ib are performed after step c and prior to step d described above; and, optionally, ii) splitting the solid support into multiple portions;
wherein the solid support comprises an intermediate formed in any one of the preceding steps, and wherein step ii) may be performed after any one or more of steps b, c, ia or ib; and, optionally, iii) hydrolyzing a solid-supported intermediate formed in the preceding step from the solid support to yield a pyruvate analog,
wherein step iii is performed immediately after any one or more of steps b and c when performed prior to step d; and, optionally iv) purifying the pyruvate-derived compound,
wherein the pyruvate-derived compound is formed after cleavage or hydrolysis of the compound from the solid support.

In another embodiment is provided a process for the synthesis of a pyruvate-derived compound, wherein the process comprises the steps of:

forming an imine at the ketone position of a pyruvic acid substituted with a leaving group at carbon 3 with a solid-supported hydroxylamine to form a solid-supported intermediate;

performing a nucleophilic substitution of the solid-supported intermediate with a compound $R^2X(H)$, wherein $R^2$ and X are as defined herein;

esterifying the solid-supported intermediate with a compound $R^1OH$ or $R^1SH$, or forming an amide with a compound $HNR^1R^{1a}$, wherein $R^1$ and $R^{1a}$ are as defined herein; and cleaving the solid-supported intermediate from the solid support to yield a pyruvate-derived compound.

In particular examples, $R^2$ is an optionally substituted phenyl, heterocycle or heteroaryl, where the heterocycle or heteroaryl contain, independently, one or more nitrogen, and/or oxygen, and/or sulfur atoms, and/or selenium, where the one or more substituent on the phenyl, heterocycle or heteroaryl is independently substituted with one or more of hydroxy, alkyl, alkenyl, alkoxy, halo, nitro, sulphonate, —CN, amino, nitrile, carboxylate, ester, amide, phosphonate, and phosphate; or, optionally substituted alkyl or alkenyl,
where the alkyl or alkenyl group is straight or branched chain, optionally substituted with one or more aryl, heteroaryl heterocyclyl, amino, hydroxy, halo, alkoxy, carbonyl, carboxylic acid, or amino acetyl; and X is N, S; or $R^2X$ is a tri-alkyl phosphite; and wherein —$R^1$ is an optionally substituted alkyl, alkenyl, cycloalkyl, aryl, alkoxy, ether, heteroaryl, heterocyclic, and alkoxyaryl, wherein when $R^1$ comprises an alkyl or alkenyl group, the alkyl or alkenyl group is optionally substituted with one or more substituents selected from the group consisting of halo, hydroxy, esters and amides; or when $R^1$ comprises a saturated or unsaturated ring, the saturated or unsaturated ring is optionally independently substituted with one or more substituents selected from the group consisting of alkyl, halo, nitro, amino, —CN, hydroxy, alkoxy, carboxylic acid, ester, and amide; and, $R^{1a}$ is —H or $R^1$.

In certain embodiment of the processes described herein, the process further comprises the step of optionally splitting the solid-supported intermediate into multiple portions after any one of the steps. In certain embodiments, the multiple portions are independently treated in the steps that follow the splitting.

In particular embodiments the cleaving step includes hydrolyzing the solid-supported intermediate from the solid support to yield a pyruvate analog.

In certain embodiments of the above-described process, the process further comprises, before the cleaving of the solid supported intermediate from the solid support, the steps of: reducing the solid-supported intermediate to an amine; and optionally acylating the solid-supported compound with a compound $R^3COL$ or alkylating with a compound $R^3CHO$ or $R^3CH_2L$, wherein L is a leaving group and $R^3$ is as defined herein, to form an O-linked solid-supported hydoxamate The process may further comprise, before the cleaving of the solid supported intermediate from the solid support, the step of: reducing the solid-supported intermediate to an amine.

Alternately, the process may further comprise, before the cleaving of the solid supported intermediate from the solid support, the steps of: reducing the solid-supported intermediate to an amine; and acylating the solid-supported compound with a compound $R^3COL$, wherein L is a leaving group and $R^3$ is as defined in the specification, to form an O-linked solid-supported hydoxamate.

In another embodiment of the above-described process, the process further comprises, before the cleaving of the solid supported intermediate from the solid support, the steps of: reducing the solid-supported intermediate to an amine; and alkylating with a compound $R^3CHO$ or $R^3CH_2L$, wherein L is a leaving group and $R^3$ is as defined in the specification, to form an O-linked solid-supported hydoxamate.

In particular embodiments, the step of esterification or amidation is done before the step of performing a nucleophilic substitution.

In certain examples of the processes described herein, the process further comprises the step of purifying the pyruvate derived compound.

In particular embodiments, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and $R^2X$— is $R^2S$—, wherein $R^2$ is alkyl; cycloalkyl; aryl; heterocyclyl or heteroaryl, said heterocyclyl or heteroaryl including one or more heteroatoms independently selected from N, S, Se, and O, and all optionally substituted with one or more substituents selected independently from the group consisting of amino, alkyl, aryl, halo, nitro, hydroxy, —CN, and sulphonate.

In another embodiment, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and $R^2X$— is $R^2N$—, wherein the N is within an 5- or 6-membered ring optionally incorporating one or two additional ring heteroatoms chosen from N, S, or O and optionally substituted with one or more substituents independently selected from the group consisting of amino, alkyl, alkoxy, aryl, halo, amide, nitro, —CN, carboxylic acid, ester, hydroxy, substituted amide, and sulphonate; or $R^2X$ is —$NHR^d$ or —$NR^d_2$, wherein $R^d$ is independently selected from the group consisting of alkyl, aminoalkyl, alkenyl, arylalkyl, and hydroxyalkyl.

In a particular embodiment of the processes described herein, $R^1$ is an optionally substituted group selected from the group consisting of $C_1$–$C_{18}$ alkyl; $C_2$–$C_8$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and $R^2X$ is a mono- or polyamino acid derivative.

In certain embodiments, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl;

$R^2X$— is $R^2S$—, wherein $R^2$ is alkyl; cycloalkyl; aryl; heterocyclyl or heteroaryl, said heterocyclyl or heteroaryl including one or more heteroatoms independently selected from N, S, Se, and O, and all optionally substituted with one or more substituents selected independently from the group consisting of amino, alkyl, aryl, halo, nitro, hydroxy, —CN, and sulphonate; and $R^3$ is optionally substituted $C_1$–$C_{18}$ alkyl, optionally substituted $C_2$–$C_{18}$ alkenyl, optionally substituted aryl, optionally substituted heteroaryl or optionally substituted heterocyclyl.

In particular examples of the processes described herein, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein the heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl;

$R^2X$— is $R^2N$—, wherein the N is within an 5- or 6-membered ring optionally incorporating one or two additional ring heteroatoms chosen from N, S, or O and optionally substituted with one or more substituents independently selected from the group consisting of amino, alkyl, alkoxy, aryl, halo, amide, nitro, —CN, carboxylic acid, ester, hydroxy, substituted amide, and sulphonate; or $R^2X$ is —$NHR^d$ or —$NR^d_2$, wherein $R^d$ is independently selected from the group consisting of alkyl, aminoalkyl, alkenyl, arylalkyl, and hydroxyalkyl, and $R^3$ is optionally substituted $C_1$–$C_{18}$ alkyl, optionally substituted $C_2$–$C_{18}$ alkenyl, optionally substituted aryl, optionally substituted heteroaryl or optionally substituted heterocyclyl.

In further examples of the processes described herein, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein the heteroatoms are selected from N, O and S;

$R^1$a is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl;

$R^2X$ is a mono- or polyamino acid derivative, and $R^3$ is optionally substituted $C_1$–$C_{18}$ alkyl, optionally substituted $C_2$–$C_{18}$ alkenyl, optionally substituted aryl, optionally substituted heteroaryl or optionally substituted heterocyclyl.

In certain aspects of the invention it can be desirable to separate, by cleavage or hydrolysis, the solid-supported intermediates described herein from the resin.

In certain aspects of the invention described herein, it is envisioned that after any one or more of the steps as described herein, the completion of the reaction may be monitored. Such monitoring includes determining whether or not the desired solid-supported intermediate has been successfully synthesized. Monitoring may be achieved by micro-cleavage of the solid-supported compound from a small sample of the solid support, and subsequent analysis of the resulting compound in either a crude, partially purified, or substantially pure form. Alternatively, monitoring may be accomplished without cleaving the solid-supported intermediate from the resin.

MODES FOR CARRYING OUT THE INVENTION

Provided are solid phase methods for the synthesis of structurally diverse pyruvate-derived compounds. The methods presented herein also encompass a parallel approach in which, after a given step the intermediates, tethered to the solid support, may be easily split and parallel synthetic pathways pursued to yield a number of different products. The methods described herein may be used to synthesize a variety of pyruvate-derived compounds, including, for example, but not limited to oximes, pyruvate analogues, modified pyruvate analogues, esters of pyruvate, including, but not limited to, polyol-pyruvate esters, pyruvate thioesters, pyruvate amides, glycerol-pyruvate esters, and dihydroxyacetone-pyruvate ester. These methods may be used with diverse classes of starting materials subsequently yielding a wide variety of functional groups.

Synthesis of such pyruvate-derived compounds on a solid support, through solid phase synthesis, has a number of advantages when compared to methods known in the art. Examples of such advantages include facile purification, ease of isolation of intermediates, monitoring of synthetic progress, the ability to easily pursue parallel synthetic pathways and therefore a powerful tool to generate a large number of structurally diverse compounds, and increased yields.

Definitions

The term "pyruvate-derived compound" refers to a compound comprising a pyruvate skeleton that may be modified or substituted at any position, and that in one embodiment may be formed from solid phase synthesis using an alpha-keto acid comprising β-leaving group. The pyruvate derived compound may be produced in accordance with the methods of the present invention.

The pyruvate-derived compound in one embodiment is a "pyruvate analogue", which is defined herein as an alpha-keto, β substituted ester, which contains a pyruvate skeleton. The term "pyruvate skeleton" refers to the (—C—C(=O)—C(=O)O—) skeleton which may be in a substituted form such as an alpha-keto acid (—CR$_x$R$_y$—C(=O)—C(=O)OR$_z$), wherein R$_x$, R$_y$ and R$_z$, if present are substituents such as H, alkyl, acyl, hydroxy, ester, aryl, halo, and other substituents known in the art and described herein.

The pyruvate-derived compound also may be a "modified pyruvate analogue" which refers to a compound comprising a modified pyruvate skeleton such as (—C—C(N)—C(=O)O) or (—C—C(=N)—C(=O)O) which may be in a substituted form such as (—Cr$_x$R$_y$—C(NR$_s$Rt)—C(=O)OR$_z$) or (—CR$_x$R$_y$—C(=NR$_s$)—C(=O)OR$_z$), wherein R$_s$, R$_t$, R$_x$, R$_y$ and R$_z$, if present, are substituents such as H, alkyl, hydroxy, ester, aryl, acyl, halo, and other substituents known in the art and described herein. Pyruvate-derived compounds includes those amides, oxime-amides and thioesters formed when Y (in R$^1$YH) is NR$^{1a}$H or S, as shown in Scheme 1 and described herein.

Unless otherwise indicated, chemical terms used have their meanings as typically known and used by those of skill in the art.

General Techniques

The practice of the present invention will employ, unless otherwise indicated, conventional techniques in the fields of synthetic organic chemistry, solid phase synthetic organic chemistry, particularly techniques such as cleavage and purification of products related to solid phase peptide synthesis using resin or solid supports, particularly Fmoc or BOC chemistry (Chan, Weng C. and White, Peter D. (2000). *Fmoc Solid Phase Peptide Synthesis: A Practical Approach*. (*Practical Approach Series*), Oxford Univ. Press), also including the use of polystyrene based resins, including modified and commercially available resins. (Burgess, K. (2000). *Solid Phase Organic synthesis*. John Wiley & Sons; and Kates, S. A. and Albericio, F. (2000). *Solid-Phase Synthesis: A Practical Guide*, Marcel Dekker).

Synthesis on a solid support and solid phase synthesis can be performed such that the synthesis from starting material to intermediates to final product is accomplished by linking at least one of the starting materials to a solid support during one of the initial synthetic steps, such as a resin bead, during synthesis from the relevant starting materials. "Solid phase synthesis" is distinguished from "solution phase synthesis" where the starting materials are dissolved in or in a mixture with solvent(s). The terms "solid support", "solid phase support" and "resin" may be used interchangeably herein. These term "resin" is as used in the art, in particular in the field of solid phase synthesis, particularly solid phase peptide synthesis. Methods for isolation, purification and characterization of the intermediates and products of the processes as described herein are known to those of skill in the art.

General references for the above techniques may also be found in Novabiochem (Calbiochem-Novabiochem Corp.) 2000 Catalog, and most recent updates; as well as numerous bibliographic publications and review articles. (Bunin, B. (1998). *Combinatorial Index*. Academic Press; Burgess, K. (2000). *Solid Phase Organic synthesis*. John Wiley & Sons; Kates, S. A.; Albericio, F. (2000). *Solid-Phase Synthesis: A Practical Guide*. Marcel Dekker).

Optionally, well known methods for the use of protecting groups and methods for deprotection may be used and are described in Atherton and Sheppard, "Solid-phase peptide synthesis—a practical approach", IRL Press at Oxford University Press, 1989; Barany, G. et al. (1987). "Solid-phase peptide synthesis: a silver anniversary report," *Int. J. Peptide Protein Res.* 30:705–739; "Solid-Phase Peptide Synthesis"(1997) *Methods in Enzymology* 289 (entire volume), Ed. Fields, G. B., Academic Press, San Diego, Calif. These references are also general references for methods of solid phase peptide synthesis.

Methods of Solid Phase Synthesis of Pyruvate-Derived Compounds

A general synthetic sequence is depicted in Scheme I. The process begins with an imine formation at the ketone position of an alpha-keto acid comprising a β-leaving group, for example, a pyruvic acid substituted with a leaving group at position 3 (e.g. bromopyruvic acid or pyruvic acid substituted by another halide including chloro- or iodo-) with a polystyrene-supported hydroxylamine (1) in the presence of trimethylorthoformate (TMOF) in THF (tetrahydrofuran). The obtained substance (2) can then be esterified or aminated with a group R$^1$— (using, for example R$^1$—YH, where Y is O, S, or NR$^{1a}$; e.g. an alcohol, R$^1$—OH; a sulfhydryl, R$^1$—SH; or an amine, R$^1$—$^{NR1a}$H; wherein the H also includes active forms such as mesylate and tosylate) with the aids of DCC (N,N'-dicyclohexylcarbodiimide) and DMAP (4-dimethylaminopyridine) in DMF (dimethylformamide). Those skilled in the art will appreciate that by substituting in Step 2 the alcohol R$^1$OH with a primary or secondary amine, corresponding amide compounds may be prepared, and by substituting the alcohol R$^1$OH with a sulfhydryl, corresponding thioesters may be formed. After esterification (including the formation of thioesters) or amidation, the resin beads can be split into multiple portions and undergo nucleophilic substitution reaction with a wide variety of $R^2X(H)$ in a parallel fashion, where X is a nucleophile and the parenthetical designator (H) indicates the optional presence of a hydrogen atom, depending on the type of nucleophile employed, as described in further detail below. $R^2X$— may also comprise other active form known in the art. As indicated in Scheme I and as will be understood by those of skill in the art, the intermediate (2) may also be treated with $R^2X(H)$ prior to esterification or amidation with a group $R^1$, with esterification or amidation being completed after the nucleophilic substitution with $R^2X(H)$ to obtain the intermediate (4). The obtained intermediate (4) can be split again into multiple portions that are subjected to either further chemical reactions and then cleaved or direct cleavage reactions. Methods for performing cleavage reactions and tailoring cleavage reactions to particular compounds and resins are well known in the art.

For example, one of the three portions can be cleaved from the resin using a TFA (trifluoroacetic acid) solution in dichloromethane (DCM) (7:3 TFA/DCM), yielding modified pyruvate analogues, 5. The second portion can be hydrolyzed from the resin, resulting in a pyruvate analog, 6. The last portion may undergo reduction with $BH_3$·pyridine to yield an amine intermediate 7. Further reductive acylation with $R^3$—CO—, wherein the starting compound further comprises a leaving group (e.g. $R^3$—COCl in Scheme I) utilizing diisopropylethylamine (DIEA) and DMAP forms an O-linked resin-bound hydroxamate 8, which is subsequently cleaved from the resin (TFA/DCM, 1:1), affording a modified pyruvate analogue 9. Alternatively, the amine intermediate 7 can be cleaved from the resin to give the product 12 as described above, or 7 can be alkylated to form the resin-bound intermediate 10 which can be subsequently cleaved from the resin to yield the product 11. Alkylation may be performed in a solvent such as DMF or an alcohol, with a reducing agent, such as, but not limited to, $NaBH_4$, or with a compound such as $R^3CH_2L$, wherein L is a leaving group, preferably a halide, for example —Cl, —Br, —F, in an inert solvent such as, but not limited to, DMF in the presence of the base such as, but not limited to, triethylamine.

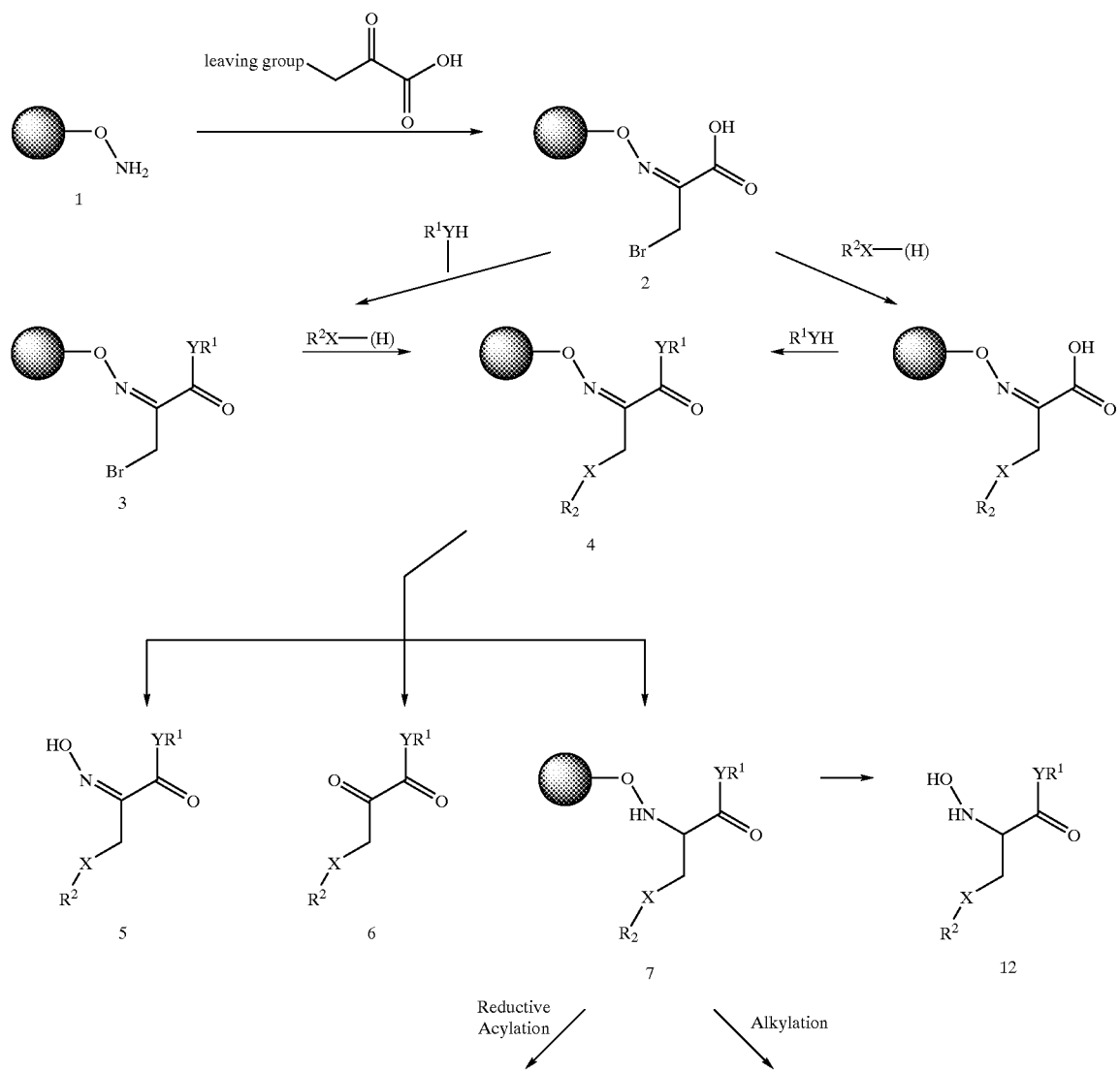

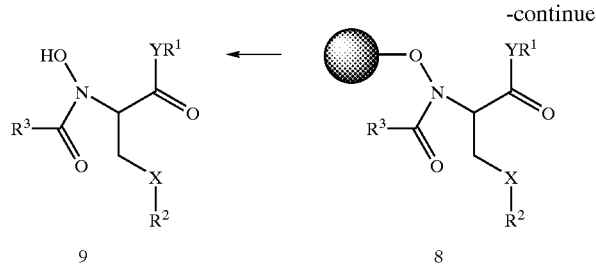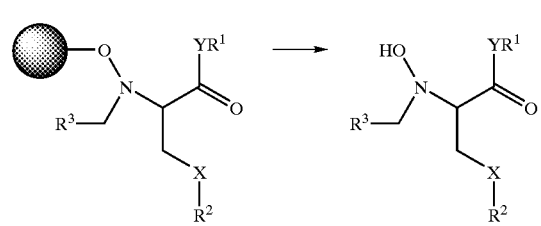

Y = O, S, NR$^{1a}$

Thus, three structurally diverse elements, for example the disclosed R-groups, can be introduced to the pyruvate-derived compounds employing this method. The first two elements are imprinted in R$^1$— and R$^2$X—, whereas the different conditions for removing pyruvate-derived compounds from the resin are the third diverse element in the case of synthesis of modified pyruvate analogue 5 and pyruvate analog 6. The third diverse element can also be incorporated by R$^3$ as shown in the case of the synthesis of a modified pyruvate analogue 9 through reductive acylation or 11 through alkylation. These three structurally diverse elements greatly increase the number and diversity of the compounds generated. For instance, if the number of different R$^1$— groups used in a split synthesis is 30, and the number of different R$^2$X-groups used in the synthesis is 30, in the case of the preparation of compound classes 5 and 6, the possible number of compounds generated could be 30×30×2 or 1,800 different compounds. For the case where a hydroxamic acid derivative 9 is prepared, when the number of different R$^3$ groups used in the synthesis is 30, the possible number of compounds generated could be 30×30×30, or 27,000 different compounds.

Compounds such as those obtained by the methods described above may be useful as dietary supplements, in clinical management of myocardial insufficiency, in prevention of adverse effects of myocardial ischemia, and in heart transplantation preservation solution components. Such compounds may also be useful in the treatment of dermatologic conditions, diabetic ketosis, myocardial ischemia, cerebral ischemia ("stroke"), injured organs and in lowering cholesterol or preventing the acute hepatic effects of ethanol. The compounds may be administered to an animal or human in an effective amount for the treatment of alleviation of a variety of therapeutic or nutritional applications.

Accordingly, in a particular embodiment is provided a method including a process for the solid phase synthesis of pyruvate-derived compounds, wherein the process comprises the steps, preferably but not necessarily, in order of a) forming an imine at the ketone position of an alpha-keto acid comprising a β-leaving group with a solid-supported hydroxylamine to form a solid-supported intermediate;

b) esterifying the solid-supported intermediate formed in step a with a compound R$^1$—OH to form an R$^1$-substituted solid-supported intermediate;

c) performing a nucleophilic substitution of the R$^1$-substituted solid-supported intermediate obtained in step b with a compound R$^2$X(H) to form an R$^2$-substituted solid-supported intermediate; and, optionally, d) cleaving the R$^2$-substituted solid-supported intermediate obtained in step c from the solid support to yield a pyruvate-derived compound.

In certain embodiments are provided methods including processes for the solid phase synthesis of pyruvate-derived compounds, wherein the processes comprises the steps, preferably but not necessarily, in order of forming an imine at the ketone position of a pyruvic acid substituted with a leaving group at carbon 3 with a solid-supported hydroxylamine to form a solid-supported intermediate;

performing a nucleophilic substitution of the solid-supported intermediate with a compound R$^2$X(H), wherein R$^2$ and X are as defined in the specification;

esterifying the solid-supported intermediate with a compound R$^1$OH or R$^1$SH, or forming an amide with a compound HNR$^1$R$^{1a}$, wherein R$^1$ and R$^{1a}$ are as defined in the specification; and, optionally cleaving the solid-supported intermediate from the solid support to yield a pyruvate-derived compound.

In certain embodiments of the above method, the nucleophlic substitution and amidation/esterification steps may be reversed such that nucleophilic substitution with R$^2$ is carried out prior to the esterification/amidation with R$^1$.

Additionally, the above-described processes may further include the step of optionally splitting the solid-supported intermediate into multiple portions after any one of the steps.

The above-described process may also further include steps to purify the end product or intermediates, including those described herein and known to those of skill in the art.

Pyruvic acid compounds which may be used to practice the methods disclosed herein may be described as a pyruvic acid substituted at the carbon 3 position with a leaving group. Leaving groups are well known in the art. Examples of such compounds include 3-bromopyruvic acid, commonly known as bromopyruvic acid, and commercially available from Aldrich (Milwaukee, Wis.). Other examples of substituted pyruvic acids of use in the methods presented herein include chloropyruvic acid and iodopyruvic acid. Other examples of good leaving groups include, but are not limited to, mesylate and tosylate.

A wide variety of compounds R$^1$YH, containing R$^1$OH, R$^1$SH, and R$^1$NR$^{1a}$H, may be used in the esterification/amidation of compound 2. For example R$^1$OH, R$^1$SH, R$^1$NR$^{1a}$H to form esters, thioesters, oxime-amides and amides, respectively, of compound 2. R$^1$YH, including R$^1$OH, R$^1$SH, and R$^1$NR$^{1a}$H, includes activated forms or protected forms. Examples are R$^1$OH which are characterized by their lipophilicity, hydrophilicity, and readiness or robustness for hydrolysis. In certain aspects, alcohols (R$^1$OH) may be used in the practice of the methods disclosed herein. In other examples of the processes described herein, amines (R$^1$NR$^{1a}$H) or sulfhydryls (R$^1$SH) may be used. In particular aspects, R$^1$— is alkyl, alkenyl, cycloalkyl, aryl, alkoxy, ether, heteroaryl, heterocyclic, and alkoxyaryl. Alkyl and alkenyl groups may be straight or branched chains.

Where R¹— includes a saturated or unsaturated ring, the ring may optionally be independently substituted with one or more —H, alkyl, halo, nitro, amino, —CN, hydroxy, alkoxy, carboxylic acid, ester, and amide. Alkyl and alkenyl groups may optionally be substituted independently with one or more groups including, but not limited to halo, hydroxy, esters, and amides. In certain embodiments, R¹— may be $C_1$-$C_{18}$ alkyl; $C_2$-$C_{18}$ alkenyl; polyethyleneglycol; aryl; including, but not limited to, phenyl; or optionally substituted phenyl, wherein the phenyl may be substituted independently with one or more groups such as alkyl (straight or branched), alkenyl (straight or branched), nitro, hydroxy, —CN, halo, or amino;

heteroaryl, including but not limited to pyrrole, furan, thiophene, quinoline, or thiazole; and cycloalkyl or heterocylic.

In certain aspects of the above described methods, R¹ may be polyethylene glycol. Particular examples of R¹— are shown below in Scheme A. Starting materials for the various substituents are commercially available from sources such as Aldrich (Milwaukee, Wis.) and/or Acros (Pittsburgh, Pa.). In the structures shown below, the terminal line (—) indicates a bond between R¹ and Y of the solid-supported intermediate 3 (Scheme I).

—R$^{1a}$ may be —H or R¹, as described herein. In certain embodiments, where R¹R$^{1a}$ are attached to a nitrogen, R¹R$^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl.

Scheme A

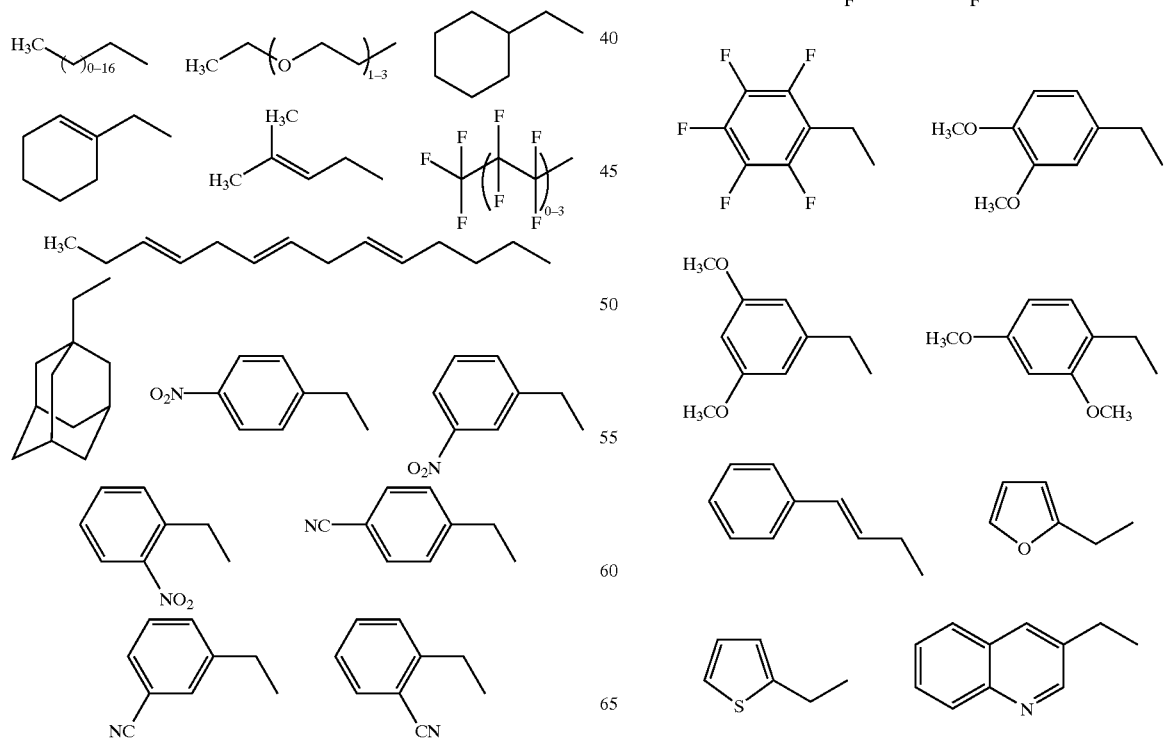

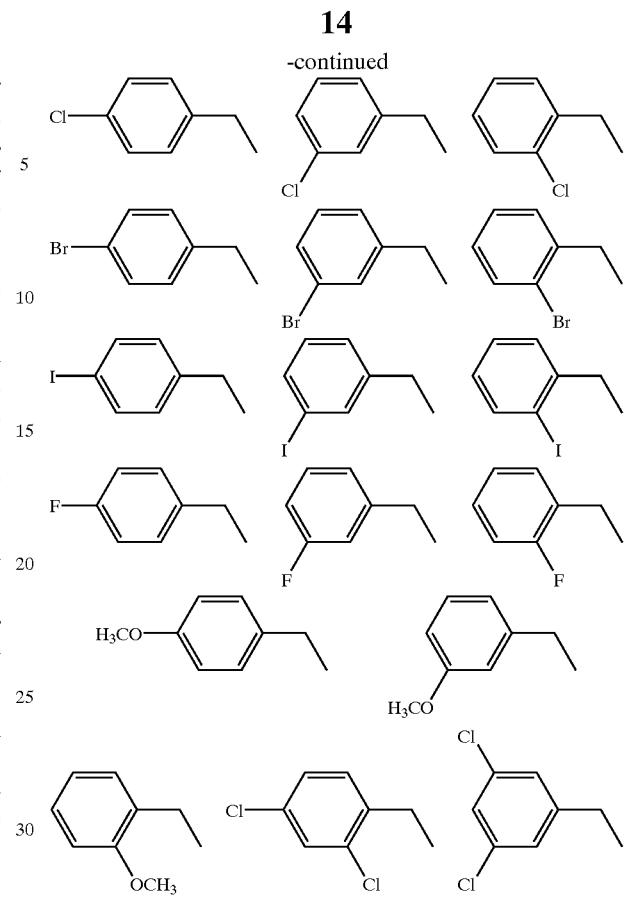

A wide variety of compounds $R^2X(H)$ may be used in the practice of the present invention. After nucleophilic substitution, a substituent $R^2X$— replaces the leaving group, e.g. —Br in Scheme I. X may be, for example, N or S. Optionally, the nucleophile can also be a $R^2X$— where X is the phosphorus atom of a tri-alkyl phosphite. The phosphite will be autooxidized after the nucleophilic substitution and exists as a phosphonate thereafter.

In the practice of the methods as described herein, in $R^2X$, where X is sulfur, $R^2$ may be, for example,

- optionally substituted heterocycle or heteroaryl, where the heterocycle or heteroaryl contain, independently, one or more nitrogen, and/or oxygen, and/or sulfur atoms, and/or selenium;
- optionally substituted phenyl; where the substituent(s) on the phenyl, heterocycle or heteroaryl may independently be one or more of —H, hydroxy, alkyl, alkenyl, alkoxy, halo, nitro, sulphonate, —CN, amino, nitrile, carboxylate, ester, amide, phosphonate, and phosphate.
- alkyl or alkenyl groups that may be straight or branched chains, optionally independently substituted with one or more aryl, heteroaryl heterocyclyl, amino, hydroxy, halo, alkoxy, carbonyl, carboxylic acid, or amino acetyl.

Particular heteroaryls include, but are not limited to, indole, imidazole, benzimidazole, benzothiazole, thiadiazole and oxadiazole.

In certain aspects the thiol may be attached to a ring via one or more methylene groups. In certain aspects, the thiol may also be part of a nucleoside, amino acid, such as cysteine, or a mono- or poly-amino acid derivative. It therefore should include all stereoisomers, tautomers, and pharmaceutically acceptable salts.

Further examples of thiol-based $R^2X$— (X is S) are shown below in Scheme B. In Scheme B, S—represents S and the bond from the S to the β-carbon of intermediate 4 in Scheme I. S is sulfur and—is the bond.

Scheme B

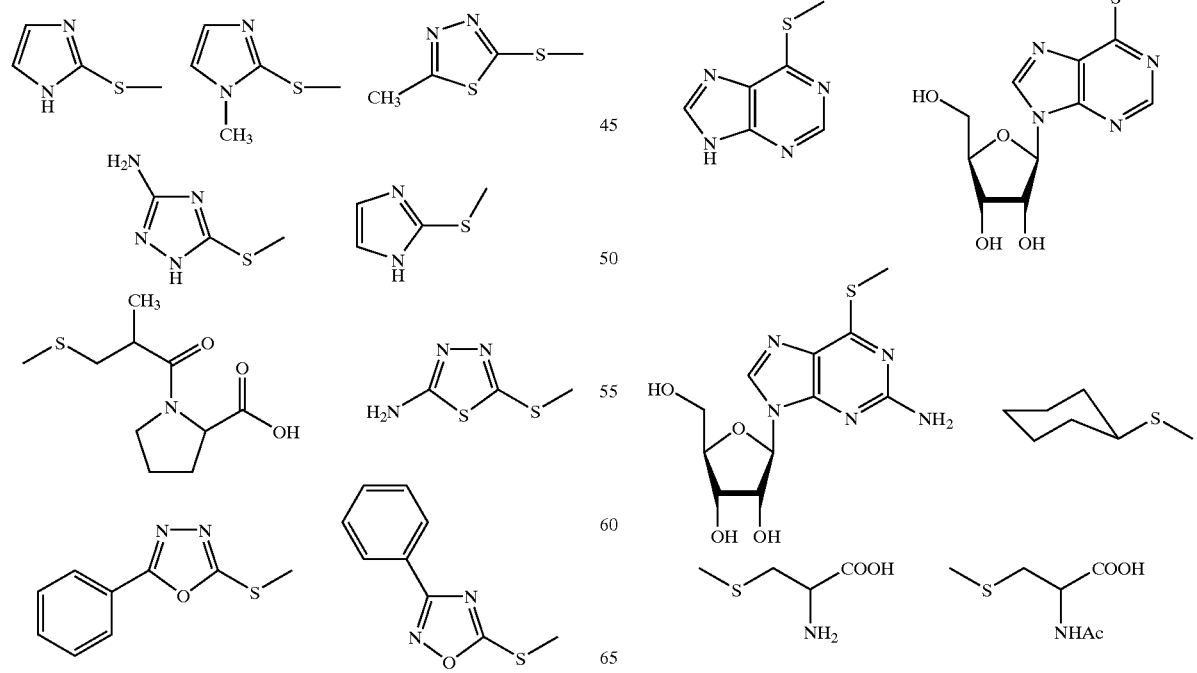

-continued

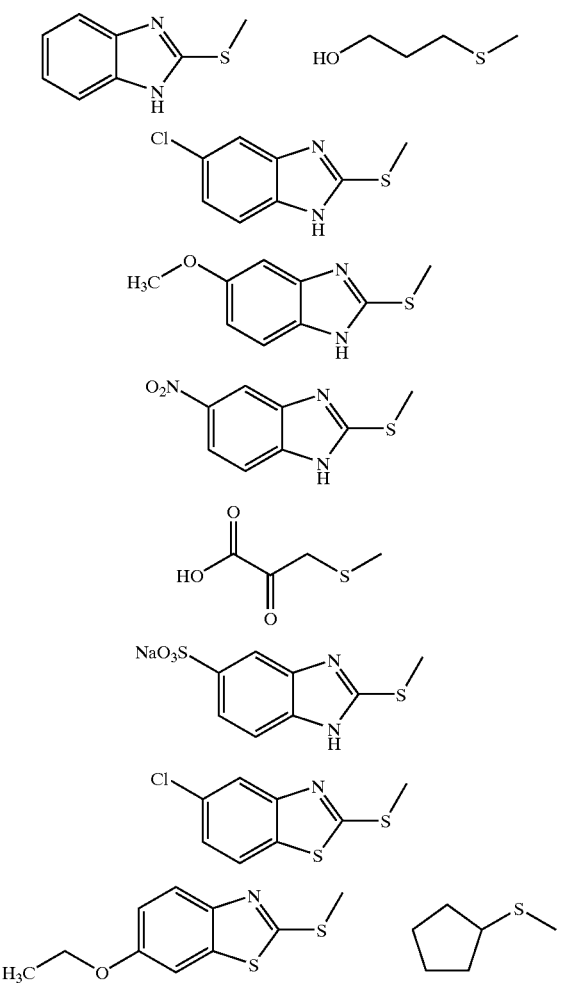

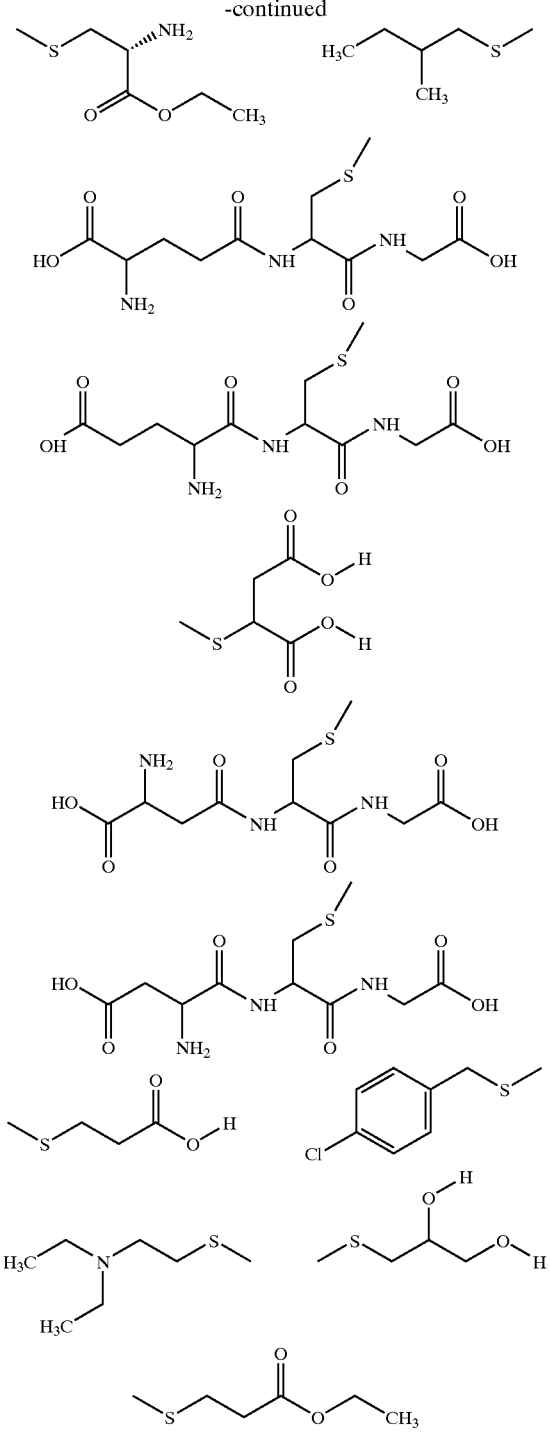

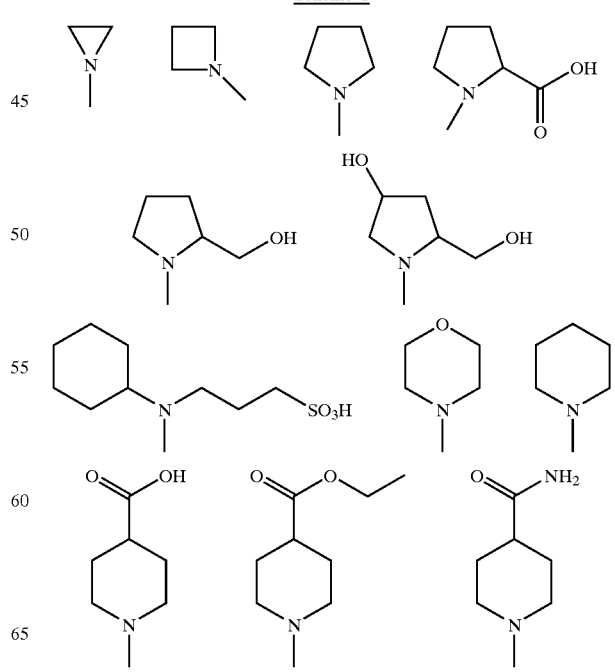

Scheme C

In certain aspects of the invention, R²X(H) may encompass (X is N), wherein the amine is contained within an optionally substituted heterocycle. In certain embodiments the heterocycle may contain additional heteroatoms such as one or more nitrogen, sulfur or oxygen atoms. In certain aspects, the heterocycle is a 3-, 4-, 5- or 6-membered ring.

In certain embodiments the heterocycle may be fused to another ring system, including cycloalkyl, substituted cycloalkyl, aryl or substituted aryl groups, wherein the aryl or cycloalkyl group may be substituted independently with one or more of the groups such as hydroxy, halo, alkyl, amino, nitro, or —CN. The heterocyle may be optionally independently substituted one or more substituents, such as, for example, —H; alkyl; halo; carbonyl (=O); —OH;

(—R$^a$OH), wherein R$^a$ is alkyl, cycloalkyl or aryl;

amide (—C(O)NH$_2$); or amino alkyl (—R$^b$N$_2$), wherein R$^b$ is alkyl; or (—C(O)OR$^{b1}$), wherein R$^{b1}$ may be —H, alkyl or alkenyl (straight or branched chain); or substituted amide (—C(O)NR$^c_2$), wherein R$^c$ is independently, alkyl; or cycloalkyl; or, a further heterocycle, wherein the heterocycle may also be optionally substituted as described above.

In certain embodiments, R²X—, wherein X is nitrogen, may also include compounds such as —NR$^d_2$, or NHR$^d$ wherein R$^d$ can be, independently, alkyl or alkenyl, either branched, cyclic or straight chain;

aryl; hydroxyalkyl (—R$^e$OH), wherein R$^e$ is straight or branched chain alkyl or alkenyl;

carboxyalkyl (—R$^f$C(O)OH), wherein R$^f$ is straight or branched chain alkyl;

sulphonic acid alkyl (—R$^f$SO$_3$H), wherein R$^f$ is straight or branched chain alkyl;

aminoalkyl (—R$^g$NR$^h_2$), wherein R$^g$ is a straight chain, branched chain or cyclic alkyl group and R$^h$ may be, independently, —H or straight or branched chain alkyl.

Particular examples of R²X— wherein X is N are shown below in Scheme C. In Scheme C, N— represents N and the bond from the N to the β-carbon of intermediate 4 in Scheme I. N is nitrogen and—is the bond. Additionally NH is a group which can be precursor to N—.

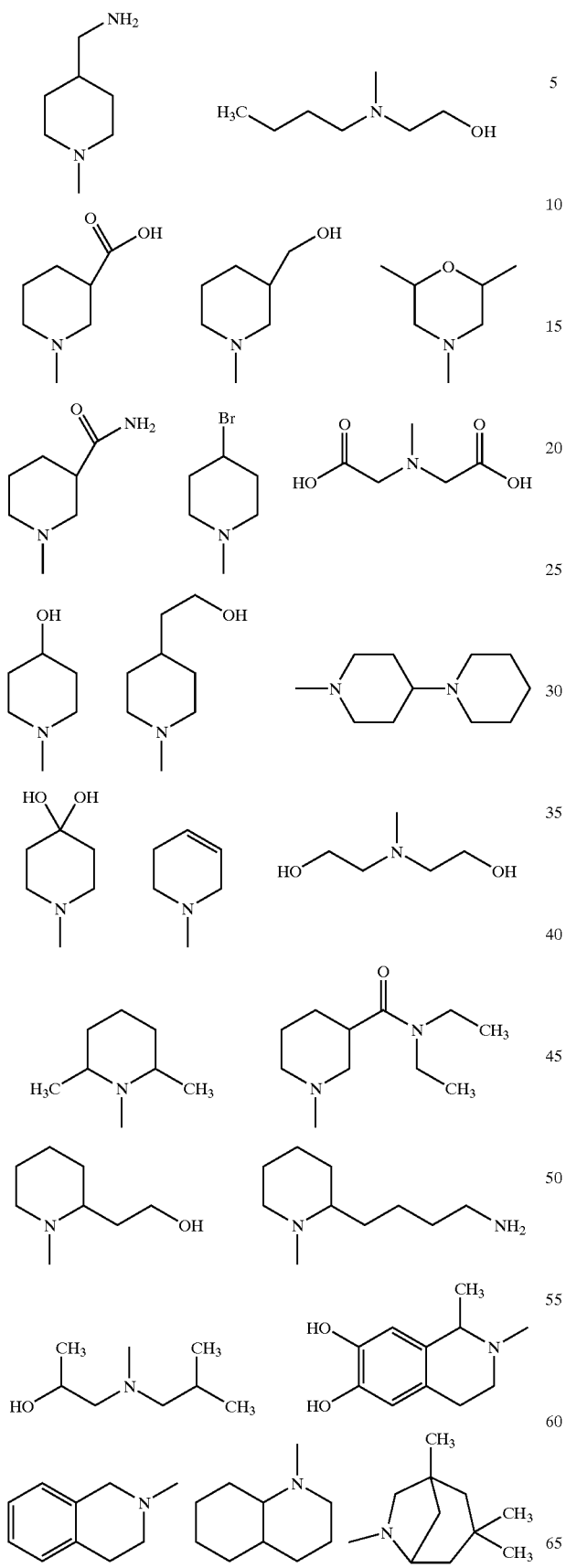
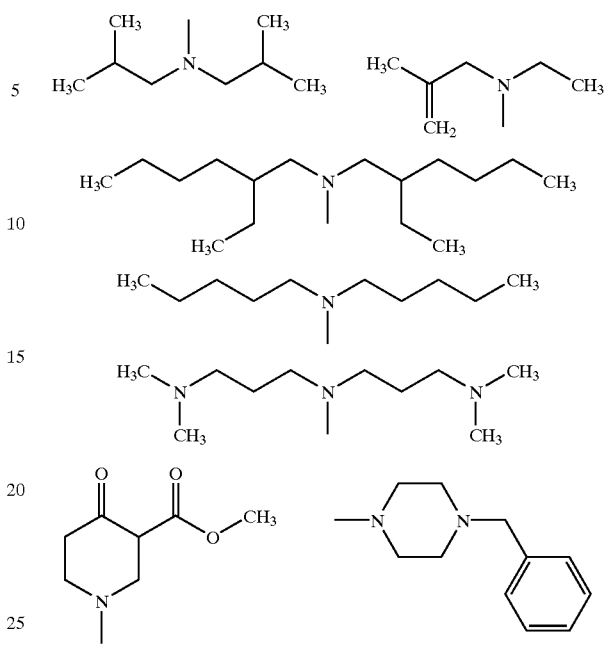

The nucleophile may also be a R²X—, trialkyl phosphite P(ORⁱ)₃; where X is the phosphorus atom of the tri-alkyl phosphite, the phosphite will be autooxidized after the nucleophilic substitution and exists as a phosphonate thereafter; wherein $R^i$ are independently selected from the group consisting of H, straight or branched chain alkyl, straight or branched chain alkenyl, aryl, straight or branched chain alkyl groups optionally substituted independently with one or more —CF₃ groups wherein the —CF₃ group is attached at the terminal carbon of the alkyl chain. In particular aspects of the methods described herein, wherein X is a phosphonate, the alkyl group is $C_1$–$C_{18}$, and the alkenyl group is $C_2$–$C_{18}$. Particular examples of R²X— as described above are shown below. In Scheme D, P—represents P and the bond connecting P to the β-carbon of intermediate 4 in Scheme I. P is phosphorus and—is the bond.

Scheme D

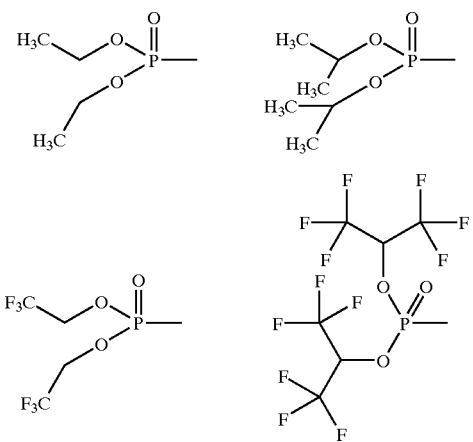

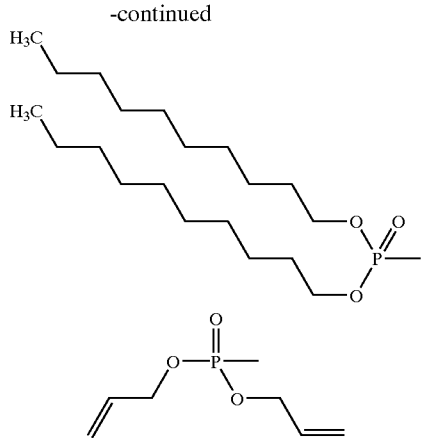

In particular aspects of the process described herein, the process includes, splitting the solid support into multiple portions,
- wherein the solid support comprises an intermediate formed in any of the preceding steps. The solid support may be split into multiple portions after any one or more of the steps described herein in which a solid-supported intermediate is formed, for example, after step b, c, or after reduction or acylation, as described below.

In certain aspects of the invention, the solid support, comprising the solid-supported intermediate may be split into at least 2, at least 3, at least 4, at least 5, at least 6, at least 7, at least 8, at least 9, at least 10, at least 15, at least 20, at least 40, least 50, at least 75, at least 90, at least 100 portions. It is understood that the term "solid-support" in this context includes the solid support as well as the intermediate which is attached to the solid support.

In a particular aspect of the invention, the process described above further comprises, after step b or c and prior to step d, the step of,
- hydrolyzing a solid-supported intermediate formed in the preceding step from the solid support to yield a pyruvate analog.

In certain embodiments of the invention as described herein, the process further comprises, after step c and prior to step d, the steps of,
- reducing the $R^2$-substituted solid-supported intermediate to an amine to form an amine-substituted solid-supported intermediate; and,
- acylating or alkylating the amine-substituted solid-supported intermediate with $R^3CO$— to form an $R^3$-substituted solid-supported intermediate.

In a particular aspect, as shown in Scheme I, the preferred reducing agent is $BH_3$— pyridine. Other reducing agents are known in the art. In a particular aspect, as shown in Scheme I, the reagents DIEA and DMAP may be used in acylating the amine-substituted solid-supported intermediate. Other reagents of use in such an acylation are known in the art.

In particular embodiments of the above-described process, acylating with $R^3CO(X)$, e.g. $R^3COCl$, followed by cleavage from the solid support yields the corresponding modified pyruvate analogue.

A wide variety of compounds $R^3CO(X)$ may be used in the above-described acylation of the solid-supported intermediate. Compounds $R^3CO(X)$ may include a leaving group (X) such as Cl (e.g. $R^3COCl$) or other halide, such as Br, I or F. Other leaving groups are known in the art.

Examples of compounds include where $R^3$ is straight, branched or cyclic $C_1$–$C_{18}$ alkyl or $C_2$–$C_{18}$ alkenyl optionally substituted with heterocyclic, heteroaryl, aryl, halo, ester, amide;
- optionally substituted aryl or heteroaryl, wherein the aryl or heteroaryl group may be independently substituted with one or more of —H, halo, straight or branched alkyl, lower alkyl, wherein lower alkyl is $C_1$–$C_6$, alkoxy, nitro, amino, —CN; or
- optionally substituted heterocycle, independently substituted with one or more alkyl; carboxy; —$CF_3$; straight or branched chain alkyl, wherein the alkyl may be optionally independently substituted with one or more of —$CF_3$, amino, nitro, hydroxy, —CN, carboxy, or alkoxy. 100721 Exemplary $R^3$ are shown below in Scheme E. In Scheme E, the terminal line (—) indicates a bond between $R^3$ and the carbonyl in intermediate 8 in Scheme I. Also in Scheme E, R may be halo, nitro, alkyl (e.g. —$CH_3$), alkoxy (e.g. —$OCH_3$) or —CN.

Scheme E

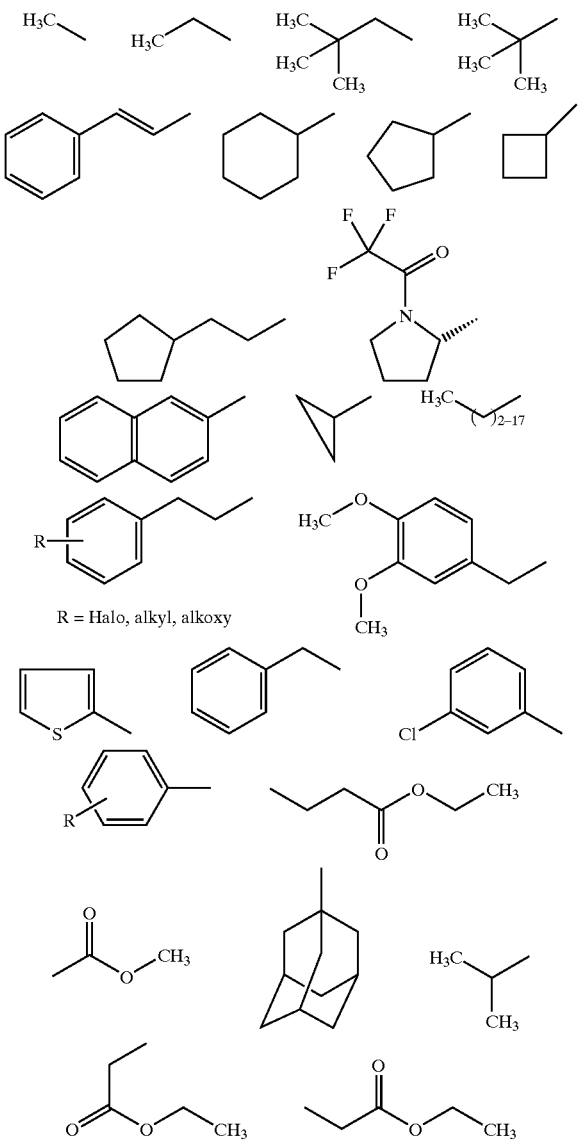

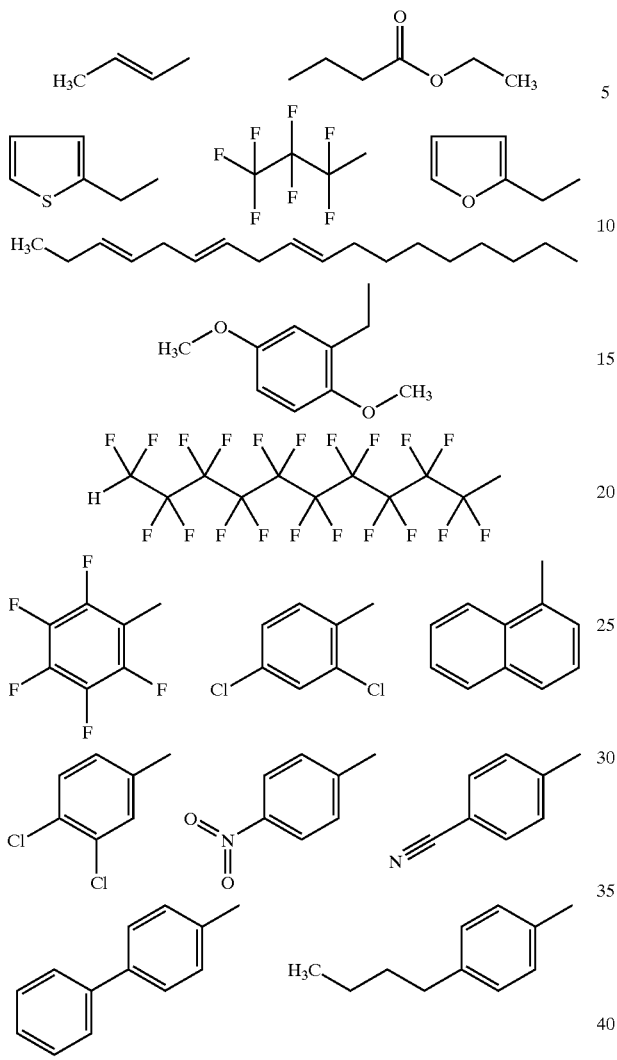

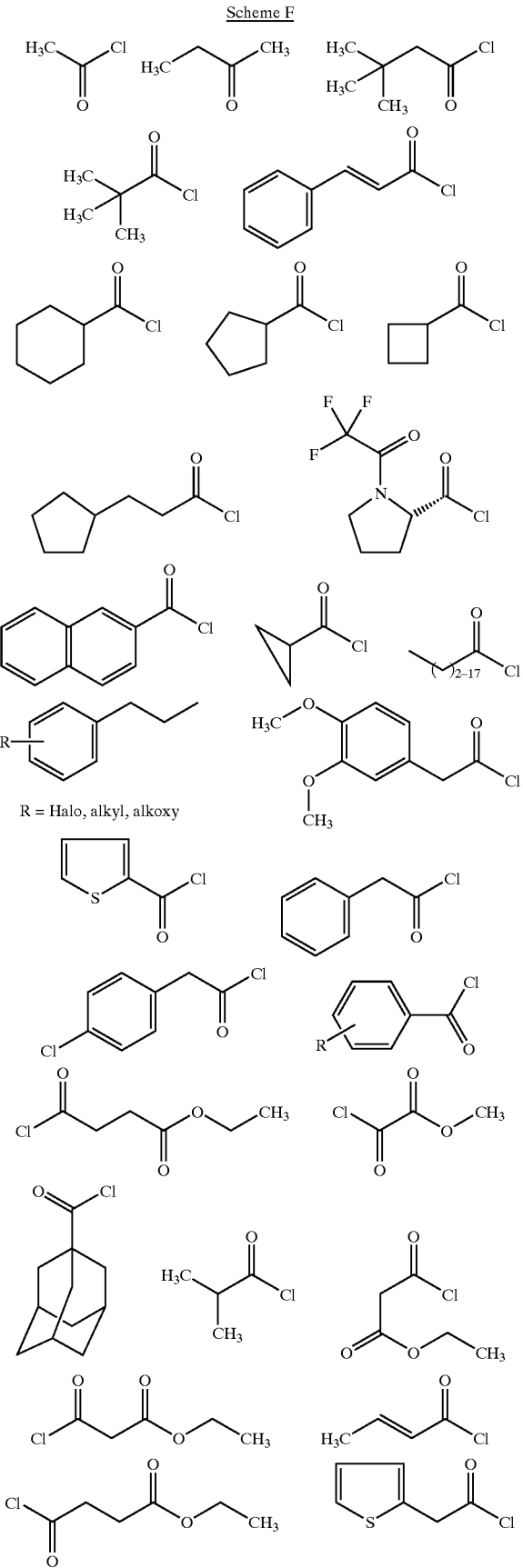

Scheme F

R = Halo, alkyl, alkoxy

In particular embodiments; acyl groups as shown below may be used in the methods described herein, wherein the acyl groups contain $R^3$. In the exemplary $R^3$-containing acyl groups shown below in Scheme F, R may be halo, nitro, alkyl (e.g. —$CH_3$), alkoxy (e.g. —$OCH_3$) or —CN.

Additionally, compounds such as $R^3CHO$ or $R^3CH_2L$, wherein L is a leaving group, may be used in to perform reductive alkylations as described in Scheme I to synthesize compounds such as compound 10, where $R^3$ are as disclosed herein. These compounds can be made by reductive alkylation from the aldehyde ($R^3CHO$) in a solvent such as DMF or an alcohol with a reducing agent, such as, but not limited to, $NaBH_4$, or with a compound such as $R^3CH_2L$, wherein L is a leaving group, preferably a halide, for example —Cl, —Br, —F, in an inert solvent such as, but not limited to, DMF in the presence of the base such as, but not limited to, triethylamine. Those of skill in the art will readily appreciate that the processes disclosed herein are not limited to the reducing agent, leaving groups, inert solvents and bases disclosed above. A skilled practitioner would be able to substitute the listed reagents for those that will function similarly in the disclosed reactions.

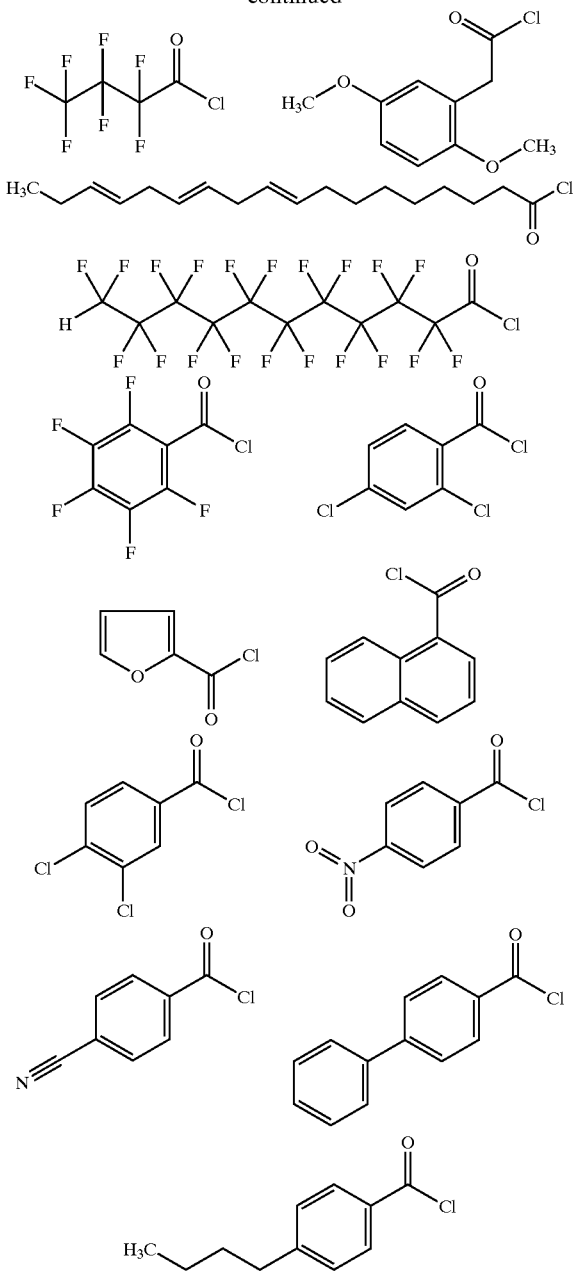

In a particular aspect of the above-described process, the pyruvate-derived compound can be, but is not limited to, an oxime, or a modified pyruvate analogue.

In particular embodiments, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and $R^2X$— is $R^2S$—, wherein $R^2$ is alkyl; cycloalkyl; aryl; heterocyclyl or heteroaryl, said heterocyclyl or heteroaryl including one or more heteroatoms independently selected from N, S, Se, and O, and all optionally substituted with one or more substituents selected independently from the group consisting of amino, alkyl, aryl, halo, nitro, hydroxy, —CN, and sulphonate.

In other embodiments, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and $R^2X$— is $R^2N$—, wherein the N is within an 5- or 6-membered ring optionally incorporating one or two additional ring heteroatoms chosen from N, S, or O and optionally substituted with one or more substituents independently selected from the group consisting of amino, alkyl, alkoxy, aryl, halo, amide, nitro, —CN, carboxylic acid, ester, hydroxy, substituted amide, and sulphonate; or $R^2X$ is —NHR$^d$ or —NR$^d_2$, wherein R$^d$ is independently selected from the group consisting of alkyl, aminoalkyl, alkenyl, arylalkyl, and hydroxyalkyl.

In a particular embodiment of the processes described herein, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and $R^2X$ is a mono- or polyamino acid derivative.

In certain embodiments, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl;

$R^2X$— is $R^2S$—, wherein $R^2$ is alkyl; cycloalkyl; aryl; heterocyclyl or heteroaryl, said heterocyclyl or heteroaryl including one or more heteroatoms independently selected from N, S, Se, and O, and all optionally substituted with one or more substituents selected independently from the group consisting of amino, alkyl, aryl, halo, nitro, hydroxy, —CN, and sulphonate; and R$^3$ is optionally substituted C$_1$–C$_{18}$ alkyl, optionally substituted C$_2$–C$_{18}$ alkenyl, optionally substituted aryl, optionally substituted heteroaryl or optionally substituted heterocyclyl.

In particular examples of the processes described herein, R$^1$ is an optionally substituted group selected from the group consisting of C$_1$–C$_{18}$ alkyl; C$_2$–C$_{18}$ alkenyl; polyethyleneglycol; aryl; cycloalkyl; heterocyclyl and heteroaryl, wherein said heterocyclyl and heteroaryl include one or more heteroatoms and wherein the heteroatoms are selected from N, O and S;

R$^{1a}$ is hydrogen or R$^1$; or

R$^1$R$^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl;

R$^2$X— is R$^2$N—, wherein the N is within an 5- or 6-membered ring optionally incorporating one or two additional ring heteroatoms chosen from N, S, or O and optionally substituted with one or more substituents independently selected from the group consisting of amino, alkyl, alkoxy, aryl, halo, amide, nitro, —CN, carboxylic acid, ester, hydroxy, substituted amide, and sulphonate; or R$^2$X is —NHR$^d$ or —NR$^d_2$, wherein R$^d$ is independently selected from the group consisting of alkyl, aminoalkyl, alkenyl, arylalkyl, and hydroxyalkyl, and R$^3$ is optionally substituted C$_1$–C$_{18}$ alkyl, optionally substituted C$_2$–C$_{18}$ alkenyl, optionally substituted aryl, optionally substituted heteroaryl or optionally substituted heterocyclyl.

In further examples of the processes described herein, R$^1$ is an optionally substituted group selected from the group consisting of C$_1$–C$_{18}$ alkyl; C$_2$–C$_{18}$ alkenyl; polyethyleneglycol; aryl; cycloalkyl; heterocyclyl and heteroaryl, wherein said heterocyclyl and heteroaryl include one or more heteroatoms and wherein the heteroatoms are selected from N, O and S, R$^{1a}$ is hydrogen or R$^1$; or R$^1$R$^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl;

R$^2$X is a mono- or polyamino acid derivative, and

R$^3$ is optionally substituted C$_1$–C$_{18}$ alkyl, optionally substituted C$_2$–C$_{18}$ alkenyl, optionally substituted aryl, optionally substituted heteroaryl or optionally substituted heterocyclyl.

In the above-described embodiments, alkyl and alkenyl groups may be straight or branched chains.

Additional steps prior to step d may be carried out on any number of the portions of solid-supported intermediate, if the solid support has been split into portions prior to step d. A number of different chemical reactions may be performed in parallel on any number of the different fractions, according to the number of fractions into which the solid-support has been split. Examples of such reactions include, but are not limited to, reduction, reductive amidation and alkylation.

In certain aspects of the inventions, the methods described herein may be used to synthesize the exemplary compounds shown below in Scheme G and in Table 1. Table 1 additionally lists the Example number in which the synthesis of the pictured compound is detailed. The Autonom name was generated using version 2.1 of the Autonom naming package within the ChemOffice® version 6.0 suite of programs by CambridgeSoft Corp. (Cambridge, Mass.)

Scheme G

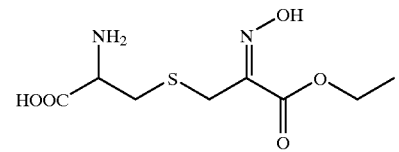

2-Amino-3-(2-ethoxycarbonyl-2-hydroxyimino-ethylsulfanyl)-propionic acid

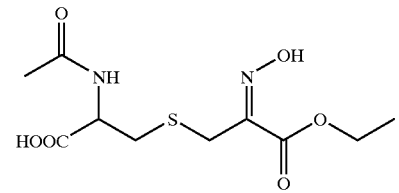

2-Acetylamino-3-(2-ethoxycarbonyl-2-hydroxyimino-ethylsulfanyl)-propionic acid

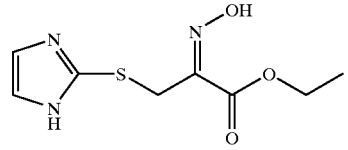

2-Hydroxyimino-3-(1H-imidazol-2-yl sulfanyl)-propionic acid ethyl ester

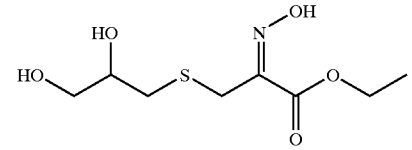

3-(2,3-Dihydroxy-propylsulfanyl)-2-hydroxyimino-propionic acid ethyl ester

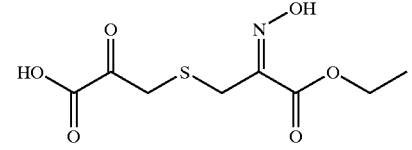

3-(2-Ethoxycarbonyl-2-hydroxyimino-ethylsulfanyl)-2-oxo-propionic acid

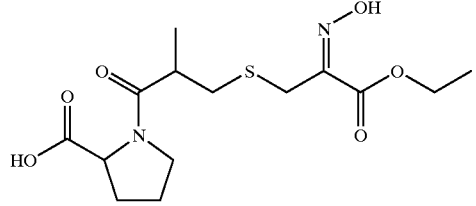

1-[3-(2-Ethoxycarbonyl-2-hydroxyimino-ethylsulfanyl)-2-methy-propionyl]-pyrrolidine-2-carboxylic acid

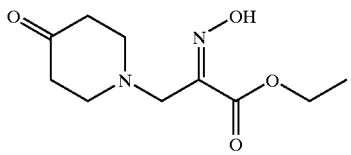

2-Hydroxyimino-3-(4-oxo-piperidin-1-yl)-propionic acid ethyl ester

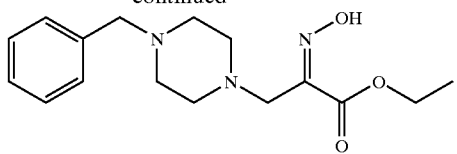

3-(4-Benzyl-piperazin-1-yl)-2-hydroxyimino
-propionic acid ethyl ester

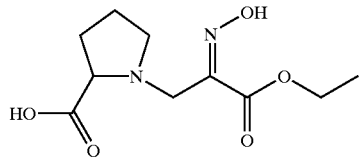

1-(2-Ethoxycarbonyl-2-hydroxyimino-
ethyl)-pyrrolidine-2-carboxylic acid

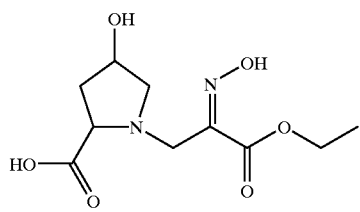

1-(2-Ethoxycarbonyl-2-hydroxyimino-ethyl)
-4-hydroxy-pyrrolidine-2-carboxylic acid

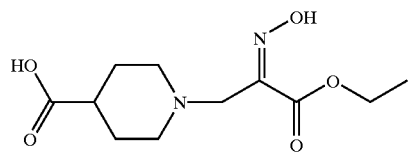

1-(2-Ethoxycarbonyl-2-hydroxyimino
-ethyl)-piperidine-4-carboxylic acid

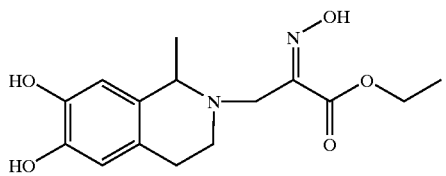

3-(6,7-Dihydroxy-1-methyl-3,4-dihydro-1H-isoquinolin
-2-yl)-2-hydroxyimino-propionic acid ethyl ester

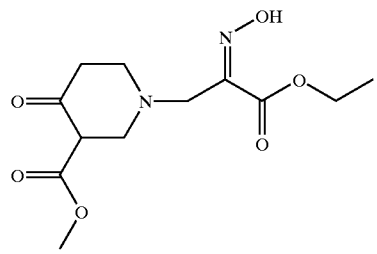

1-(2-Ethoxycarbonyl-2-hydroxyimino-
ethyl)-4-oxo-piperidine-3-carboxylic
acid methyl ester

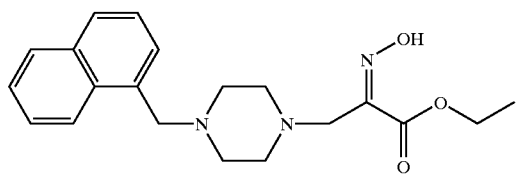

2-Hydroxyimino-3-(4-naphthalen-1-ylmethyl-piperazin
1-yl)-propionic acid ethyl ester

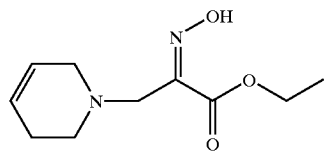

3-(3,6-Dihydro-2H-pyridin-1-yl)-
2-hydroxyimino-propionic acid ethyl ester

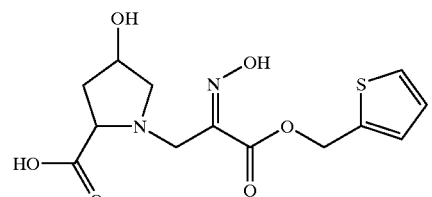

4-Hydroxy-1-[2-hydroxyimino-2-(thiophen-2-yl
methoxycarbonyl)-ethyl]-pyrrolidine-2-carboxylic acid

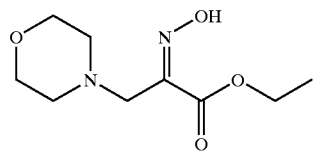

2-Hydroxyimino-3-morpholin-4-yl-propi
onic acid ethyl ester

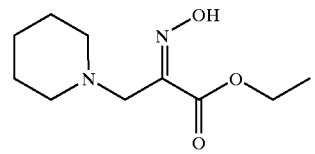

2-Hydroxyimino-3-piperidin-1-yl-propionic acid ethyl ester

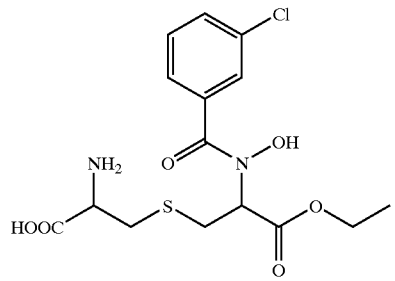

2-Amino-3-{2-[(3-chloro-benzoyl)-hydroxy
-amino]-2-ethoxycarbonyl-ethylsulfanyl}-propionic acid

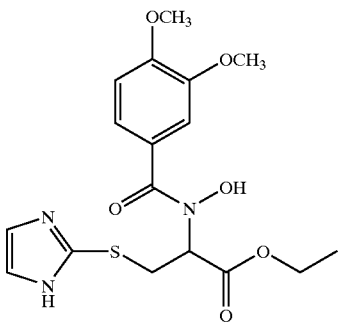

2-[(3,4-Dimethoxy-benzoyl)-hydroxy-amino]-3
-(1H-imidazol-2-ylsulfanyl)-propionic acid ethyl ester -continued

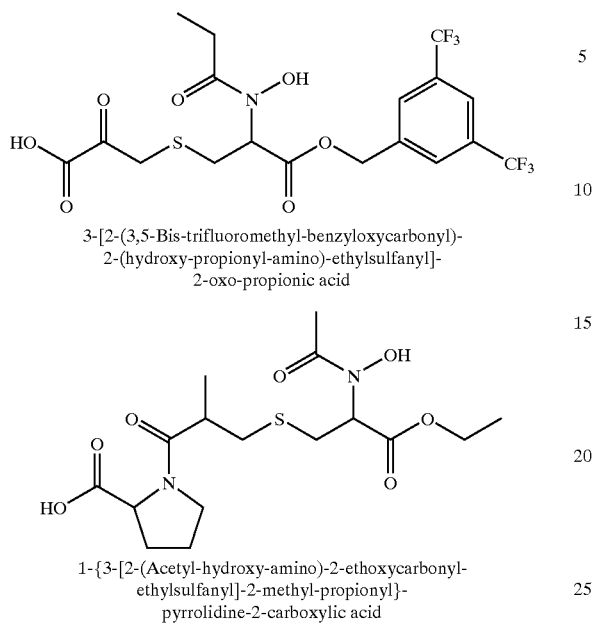

3-[2-(3,5-Bis-trifluoromethyl-benzyloxycarbonyl)-
2-(hydroxy-propionyl-amino)-ethylsulfanyl]-
2-oxo-propionic acid 1-{3-[2-(Acetyl-hydroxy-amino)-2-ethoxycarbonyl-
ethylsulfanyl]-2-methyl-propionyl}-
pyrrolidine-2-carboxylic acid

TABLE 1

Exemplary Compounds

| EX # | STRUCTURE | Autonom Name | M + H |
|---|---|---|---|
| 4 | | 2-Hydroxyimino-3-p-tolylsulfanyl-propionic acid | 226 |
| 4 | | 2-Hydroxyimino-3-piperidin-1-yl-propionic acid | 187 |
| 5 | | 2-Hydroxyimino-3-p-tolylsulfanyl-propionic acid methyl ester | 240 |
| 5 | | 2-Hydroxyimino-3-p-tolylsulfanyl-propionic acid ethyl ester | 254 |

TABLE 1-continued

Exemplary Compounds

| EX # | STRUCTURE | Autonom Name | M + H |
|---|---|---|---|
| 5 | | 2-Hydroxyimino-3-piperidin-1-yl-propionic acid ethyl ester | 215 |
| 5 | | 2-Hydroxyimino-3-morpholin-4-yl-propionic acid ethyl ester | 217 |
| 5 | | 2-Hydroxyimino-3-(4-oxo-piperidin-1-yl)-propionic acid ethyl ester | 229 |
| 5 | | 2-Hydroxyimino-3-(4-hydroxy-piperidin-1-yl)-propionic acid ethyl ester | 231 |
| 5 | | 1-(2-Ethoxycarbonyl-2-hydroxyimino-ethyl)-pyrrolidine-2-carboxylic acid | 245 |
| 5 | | 3-(4-Benzyl-piperazin-1-yl)-2-hydroxyimino-propionic acid ethyl ester | 306 |
| 5 | | 3-[Bis-(2-hydroxy-ethyl)-amino]-2-hydroxyimino-propionic acid ethyl ester | 235 |
| 5 | | 1-[3-(2-Ethoxycarbonyl-2-hydroxyimino-ethylsulfanyl)-2-methyl-propionyl]-pyrrolidine-2-carboxylic acid | 329 |

TABLE 1-continued

Exemplary Compounds

| EX # | STRUCTURE | Autonom Name | M + H |
|---|---|---|---|
| 5 | 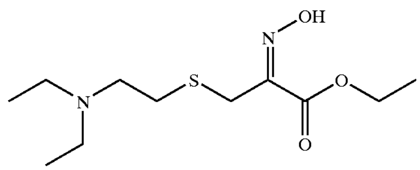 | 3-(2-Diethylamino-ethylsulfanyl)-2-hydroxyimino-propionic acid ethyl ester | 263 |
| 6 | | 1-Piperidin-1-yl-3-p-tolylsulfanyl-propane-1,2-dione 2-oxime | 293 |
| 6 | | 2-Hydroxyimino-N-phenyl-3-p-tolylsulfanyl-propionamide | |
| 6 | | 3-(2-Diethylamino-ethylsulfanyl)-2-hydroxyimino-N-phenyl-propionamide | 302 |
| 6 | | 1,3-Di-piperidin-1-yl-propane-1,2-dione 2-oxime | 254 |
| 6 | | 3-Morpholin-4-yl-1-piperidin-1-yl-propane-1,2-dione 2-oxime | 256 |
| 6 | | 3-(4-Benzyl-piperazin-1-yl)-1-piperidin-1-yl-propane-1,2-dione 2-oxime | 345 |
| 7 | | 2-Hydroxyimino-3-piperidin-1-yl-thiopropionic acid S-(2-hydroxy-ethyl) ester | 247 |
| 7 | | 2-Hydroxyimino-3-morpholin-4-yl-thiopropionic acid S-(2-hydroxy-ethyl) ester | 249 |

TABLE 1-continued

Exemplary Compounds

| EX # | STRUCTURE | Autonom Name | M + H |
|---|---|---|---|
| 7 | (structure) | 3-(4-Benzyl-piperazin-1-yl)-2-hydroxyimino-thiopropionic acid S-(2-hydroxy-ethyl) ester | 338 |

In certain aspects of the process as described herein, the process may further comprise, after step d, the step of, e) purifying the pyruvate-derived compound.

Step e may also be performed after step d, where step d comprises hydrolyzing the solid-supported intermediate. Means of purifying the product compound or synthetic intermediates are well known to those of skill in the art. Purification may include filtration and solvent washes of the resin, for example to remove unreacted reagents. Suitable solvents include, but are not limited to, DCM, DMF, MeOH, and THF. Washes may be performed after any number of the steps of the methods described herein.

Washes may also be included as part of the synthetic method, for example, for the purpose of increasing the yield of individual steps. Washes may be performed at least 1x, at least 2x, at least 3x, at least 4x, at least 5x, at least 6x, at least 7x, at least 8x, at least 9x, at least 10x. Washes may include single or multiple washes of a variety of solvents, including solutions of multiple solvents. Wash volumes may be varied according to the scale of the synthesis, the nature of the reaction performed and other factors as is known by those of skill in the art. For example the wash volume may be at least 1 ml, at least 2 ml, at least 3 ml, at least 5 ml, at least 10 ml, at least 15 ml, at least 20 ml, at least 50 ml, at least 75 ml, at least 100 ml, at least 200 ml, at least 300 ml, at least 500 ml, at least 1 L. In certain embodiments of the methods described herein, 3–5 washes of 10 ml/g may be performed.

In certain aspects purification may be accomplished by, but is not limited to, any of the following techniques; preparative HPLC (high performance liquid chromatography), including reverse phase HPLC; silica gel chromatography, preparative TLC (Thin Layer Chromatography), ion exchange chromatography, evaporation/crystallization, precipitation, either in air or under vacuum.

In certain aspects of the invention described herein, it is envisioned that after any one or more of the steps as described herein, the completion of the reaction may be monitored. Such monitoring includes determining whether or not the desired solid-supported intermediate has been successfully synthesized. Monitoring may be achieved by micro-cleavage of the solid-supported compound from a small sample of the solid support, and subsequent analysis of the resulting compound in either a crude, partially purified, or substantially pure form. Alternatively, monitoring may be accomplished without cleaving the solid-supported intermediate from the resin. Methods for analyzing the formation of the solid-supported intermediate or mixtures of solid-supported intermediates include those as described herein before for analysis of the final desired compounds. Other methods for use in monitoring the success of the reaction include tests for the incorporation of particular functional groups and are well known in the art. Such methods may include may include NMR, GC, HPLC, LC/MS, MS, UV, IR, elemental analysis, Kaiser test, TNBS (trinitrobenzene sulfonic acid) test, and chloranil test. Certain of these methods may also be performed without cleaving the solid-supported intermediate from the solid support, such as IR, elemental analysis, Kaiser test, TNBS (trinitrobenzene sulfonic acid) test, and chloranil test.

Synthetic intermediates may also be cleaved from the solid support after any of the synthetic steps, and isolated in a crude, partially purified, or substantially pure form, according to the methods described herein and those known in the art.

Solid Supports

The solid phase supports used are O-linked hydroxylamine resins and can be made using methods of the known art. Particularly, Wang resin and five halogenated polystyrene-based resins are suitable for the production of the solid phase supports. These halogenated resins include Merrifield resins, ParaMax Merrifield resins, brominated Wang resins, TentaGel resins (polyethylene glycol (PEG) modified Wang resins), and a trityl chloride resin. Merrifield and Wang resins are commercially available from Novabiochem/Calbiochem-Novabiochem Corp. (La Jolla, Calif.) and Advanced ChemTech (Louisville, Ky.). The preparation of the O-hydroxylamine linked resin is illustrated in Scheme II.

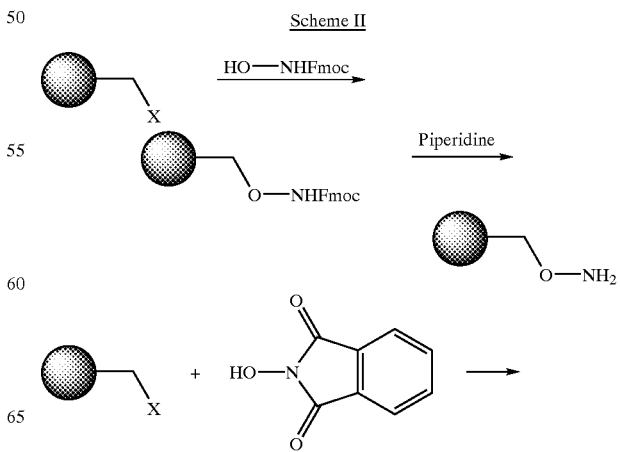

Scheme II

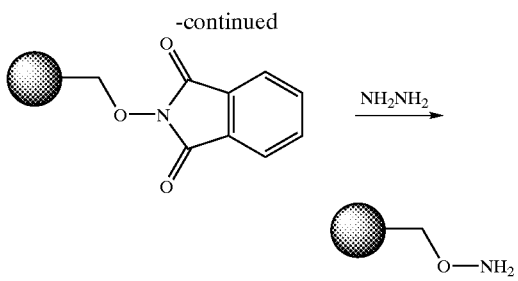

Where X is Cl, the resin is either a Merrifield or ParaMax Merrifield resin. Where X is Br, the resin is either a TentaGel or Wang resin. Alternatively a trityl chloride resin (shown below) may also be used.

The hydroxylamine moiety is incorporated onto the resin using either a 9-fluorenylmethoxycarbonyl (Fmoc) masked hydroxylamine or N-hydroxyl phthalimide in the presence of NaH and followed by either removal of Fmoc using piperidine or cleave phthalimide using hydrazine ($NH_2NH_2$).

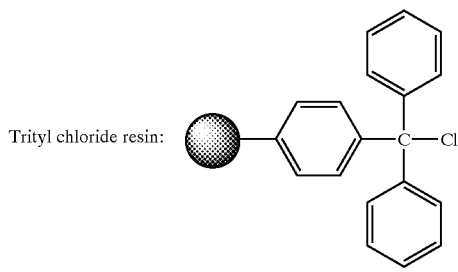

Alternatively, the O-linked hydroxylamine resin can also be made directly from Wang resin utilizing a Mitsunobu condition (Floyd, C. D.; Lewis, D. N.; Patel, S. R.; Whittaker, M. (1996) *Tetrahedron Lett.* 37:8045–8048) as shown in Scheme III.

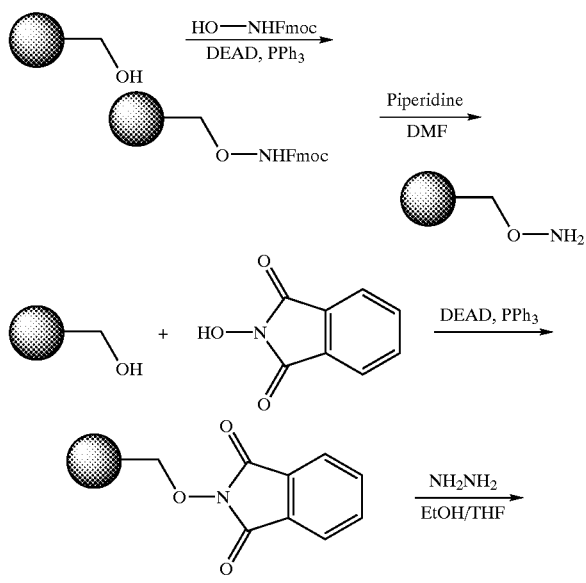

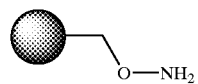

In one embodiment, a Wang resin-based hydroxylamine solid phase support is resin used for the current application.

All references, patents and patent applications disclosed herein are hereby incorporated in their entirety.

The invention will be further understood by the following non-limiting examples.

EXAMPLES

Materials

Most solvents and reagents are purchased from Aldrich (Milwaukee, Wis.), Sigma (St. Louis, Mo.), Acros Organics International (Pittsburgh, Pa.), and Fluka (Milwaukee, Wis.). Solvents and reagents were used as received without further purification. Polystyrene solid phase support materials were from either Advanced ChemTech (Louisville, Ky.) or Novabiochem (La Jolla, Calif.).

Example 1

A 50-mL fritted polypropylene syringe is charged with O-linked resin-bound hydroxylamine (1.0 g, 1.4 mmol/g). A solution of 3-bromopyruvic acid (1.67 g, 14 mmol), acetic acid (0.29 mL, 5.0 mmol), and trimethylorthoformate (TMOF) (12 mL) in THF (20 mL) is introduced, and the mixture is agitated at room temperature for 18 h. The solution is drained and the procedure is repeated for an additional 18 h until the reaction is complete as indicated by Kaiser test. After the solution is drained again, the resin is washed with dichloroethane (DCE) (3×), DMF (dimethylformamide) (5×), and DCM (dichloromethane) (3×).

A solution of alcohol $R^1$—OH (14 mmol), DCC (14 mmol), and DMAP (0.7 mmol) in DCM (20 mL) is added, and the mixture is agitated at room temperature for 18 h. The solution is drained and the procedure is repeated for another 6 h. After the solution is drained, the resin is washed with DCM (5×). To this derivatized resin suspended in DCM (20 mL) is added the nucleophile $R^2X$— (14 mmol). The mixture is shaken at room temperature for 18 h and then the solution is drained to allow a repeat of the procedure for an additional 6 h. The resin is filtered and then washed with DCM (5×). After drying under high vacuum the resin undergoes the following operations.

A portion of the resin is treated with a mixture of TFA (trifluoroacetic acid) and DCM (7:3, 30-mL/g resin) with agitation for 30 min. The resin is filtered off and the solution is evaporated under reduced pressure to afford the pyruvate-oxime (modified pyruvate analogue).

Another portion of the resin is treated with a solution of $TiCl_3$ (0.1 M) in TFA and water (1:1) for 3 h. The resin is filtered off and the solution is evaporated to dryness. The residue dissolved in DCM is passed through a short silica gel column, giving a pyruvate analogue.

The third portion of the resin is treated with $BH_3$-pyridine (8 M, 1.5 eq) and DCM. The mixture is cooled to 0° C. and dichloroacetic acid (2 eq) is added dropwise. The vessel is capped and the mixture is shaken for 18 h. The resin is filtered off and washed with DCM (2×), MeOH (1×), shaken with MeOH for 30 min followed by draining and washing with MeOH (1×), DMF (4×), and DCM (5×).

The resin thus obtained is treated with a solution of acyl chloride (10 eq), DIEA (diisopropylethylamine) (10 eq), and DMAP (0.05 eq) in DCM. The mixture is agitated at room temperature for 18 h, then the resin is drained, washed with DCM (4×), DMF (4×), and DCM (4×), and dried under vacuum overnight. To this resin is added a solution of TFA/DCM (1:1). The mixture is shaken at room temperature for 2 d then the solvent is evaporated to afford a crude hydroxamic acid (modified pyruvate analogue) product.

The final products are characterized with conventional analytical means such as, NMR, LC/MS, and elemental analysis.

Example 2

O-alkyl Hydroxylamine Loaded Resin

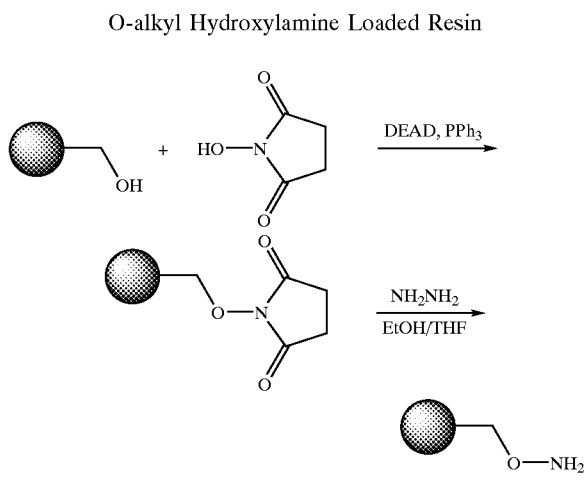

Wang resin [4-(hydroxymethyl) phenoxymethyl copolystyrene], (5.0 g, 6.5 mmol; substitution=1.3 mmol/g) was suspended in anhydrous THF (70 mL) and gently agitated for 30 min under a nitrogen atmosphere. N-Hydroxy succinimide (1.12 g, 9.75 mmol) followed by triphenyl phosphine (2.56 g, 9.75 mmol) was added and the suspension was agitated until the reagents dissolved. Additionally, diisopropyl azodicarboxylate (1.97 g, 9.75 mmol) was slowly added at 0° C. The mixture was allowed to slowly come to ambient temperature and was agitated overnight. The resin was filtered, washed successively with 20 mL each of THF, DMF, CH$_2$Cl$_2$, MeOH and CH$_2$Cl$_2$, and dried under vacuum to a constant weight.

The resin was then suspended in a 1:1 mixture of THF/MeOH (100 mL total) which was treated with hydrazine (98%, 10 mL, large excess) at 0° C., slowly warmed to ambient temperature and agitated overnight. The resin was filtered, washed successively with 20 mL each of DMF, CH$_2$Cl$_2$, MeOH and CH$_2$Cl$_2$, and dried under vacuum to a constant weight. The resulting O-alkyl hydroxylamine-loaded resin was assumed to have 1.3 mmol/g substitution based on the substitution of the starting resin.

Example 3

Condensation of 3-Bromopyruvic Acid with Resin-bound Hydroxylamine

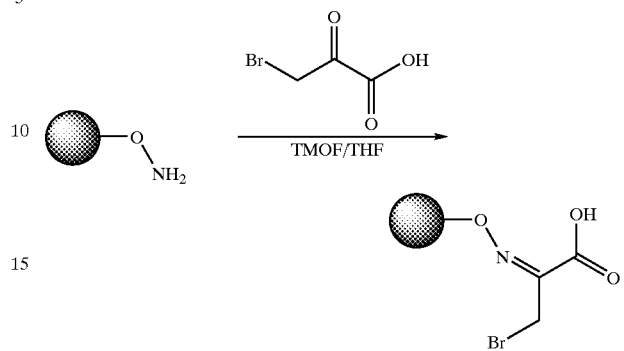

The resin, as prepared in Example 3 above, (1.0 g, 1.3 mmol) was suspended in a 2:1 mixture of MeOH and CH$_2$Cl$_2$ (30 mL) to which was added acetic acid (0.5 mL) followed by 3-bromopyruvic acid (1.11 g, 6.65 mmol), and the suspension was agitated for 3 hrs. The resin was then filtered, washed successively with 20 mL each of CH$_2$Cl$_2$, MeOH, and CH$_2$Cl$_2$ and dried under vacuum to a constant weight.

Example 4

2-Hydroxyimino-3-p-tolylsulfanyl-propionic Acid

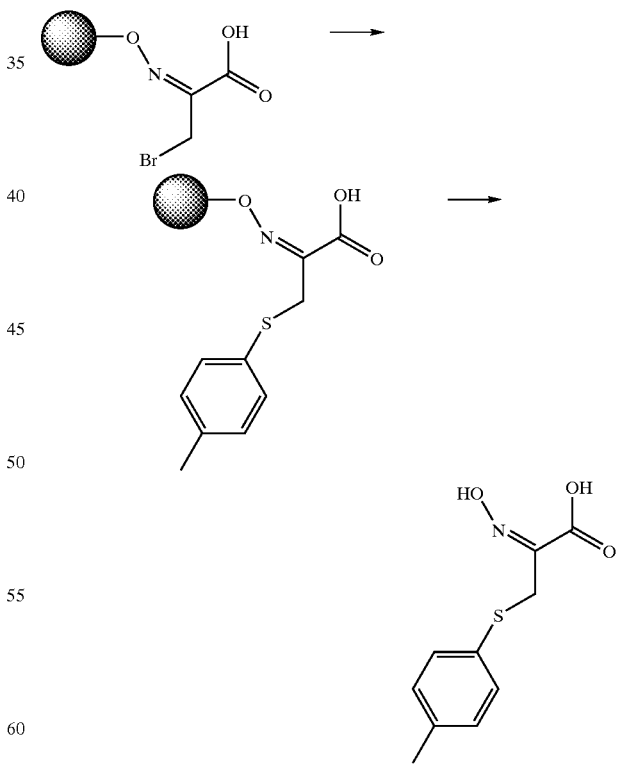

The resin, loaded as described in Example 3, (1.0 g, 1.3 mmol) was suspended in CH$_2$Cl$_2$ (25 mL) and agitated for 30 min for swelling. Triethylamine (1 mL, large excess) followed by 4-thiocresol (0.83 g, 6.64 mmol) was added and the suspension was agitated for 3 hrs. The resin was then filtered, washed successively with 20 mL each of CH$_2$Cl$_2$, MeOH and CH$_2$Cl$_2$, and dried under vacuum to a constant weight.

The resin was suspended in a mixture of TFA and CH$_2$Cl$_2$ (1:3, 25 mL total volume, and agitated for 1 hr. The resin was filtered off, washed with CH$_2$Cl$_2$ (10 mL), and the combined organic filtrates were concentrated to yield 2-hydroxyimino-3-p-tolylsulfanyl-propionic acid as a white solid (260 mg). MS (ESI) m/z: 226 [M+H].

Similarly, following the procedure as described above, but replacing thiocresol with piperidine and utilizing, if needed, modifications known to those skilled in the art 2-hydroxyimino-3-piperidin-1-yl-propionic acid (MS (ESI) m/z: 187 [M+H]) was prepared.

Example 5

2-Hydroxyimino-3-p-tolylsulfanyl-propionic Acid Methyl Ester

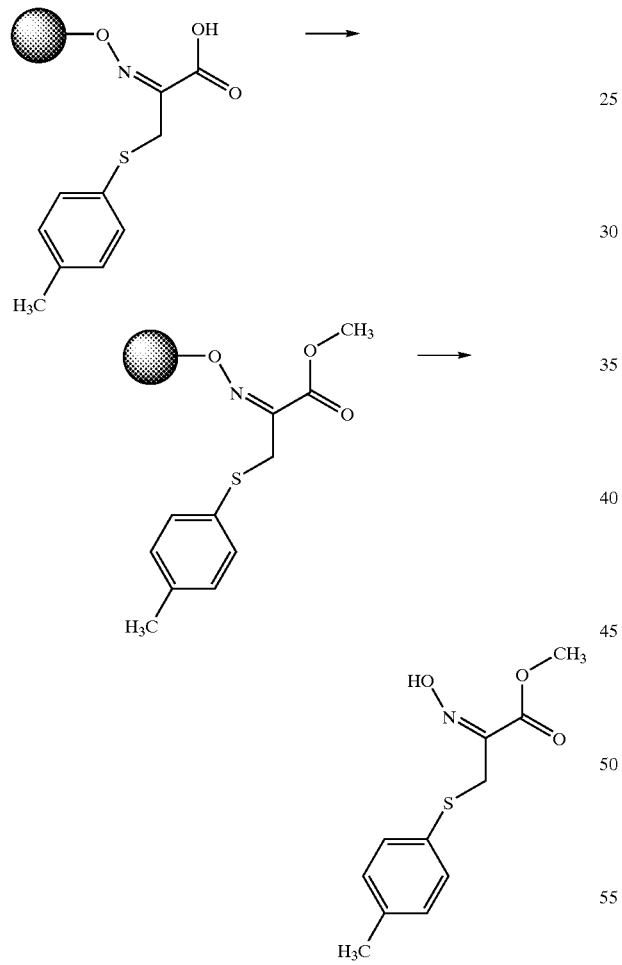

The pre-loaded Wang resin prepared as in Example 3 (0.5 g, 0.665 mmol) was suspended in CH$_2$Cl$_2$ (20 mL) to which was added a solution of hydroxy benzotriazole (0.45 g, 3.325 mmol) in DMF (10 mL), followed by the addition of a solution of diisopropyl carbodiimide (0.42 g, 3.325 mmol) in CH$_2$Cl$_2$ (5 mL). The suspension was agitated for 10 min. Methanol (1.0 mL) was then added and the suspension agitated for 3 hrs. The resin was filtered, washed successively with DMF and CH$_2$Cl$_2$ to yield resin-bound 2-hydroxyimino-3-p-tolylsulfanyl-propionic acid methyl ester, which was dried under vacuum to a constant weight.

The resin was suspended in a mixture of TFA and CH$_2$Cl$_2$ (1:3, 25 mL total volume) and agitated for 1 hr. The resin was filtered off, washed with CH$_2$C$_{12}$ (10 mL), and the combined organic filtrates were concentrated to yield 2-hydroxyimino-3-p-tolylsulfanyl-propionic acid methyl ester as a brown oil (130 mg,). MS MS (ESI) m/z: 240 [M+H]

The compounds listed below were synthesized using the procedure described above for the preparation of 2-hydroxyimino-3-p-tolylsulfanyl-propionic acid methyl ester. The procedure was modified by replacing methanol with an appropriate alcohol derivative. Where necessary, modifications known to those skilled in the art the were employed to synthesize the following:

2-Hydroxyimino-3-p-tolylsulfanyl-propionic acid ethyl ester, MS (ESI) m/z: 254 [M+H];
2-Hydroxyimino-3-piperidin-1-yl-propionic acid ethyl ester, MS (ESI) m/z: 215 [M+H];
2-Hydroxyimino-3-morpholin-4-yl-propionic acid ethyl ester, MS (ESI) m/z: 217 [M+H];
2-Hydroxyimino-3-(4-oxo-piperidin-1-yl)-propionic acid ethyl ester, MS (ESI) m/z: 229 [M+H];
2-Hydroxyimino-3-(4-hydroxy-piperidin-1-yl)-propionic acid ethyl ester, MS (ESI) m/z: 231 [M+H];
1-(2-Ethoxycarbonyl-2-hydroxyimino-ethyl)-pyrrolidine-2-carboxylic acid, MS (ESI) m/z: 245 [M+H];
3-(4-Benzyl-piperazin-1-yl)-2-hydroxyimino-propionic acid ethyl ester, MS (ESI) m/z: 306 [M+H];
3-[Bis-(2-hydroxy-ethyl)-amino]-2-hydroxyimino-propionic acid ethyl ester, MS (ESI) m/z: 235 [M+H];
1-[3-(2-Ethoxycarbonyl-2-hydroxyimino-ethylsulfanyl)-2-methyl-propionyl]-pyrrolidine-2-carboxylic acid, MS (ESI) m/z: 329 [M+H–H$_2$O]; and
3-(2-Diethylamino-ethylsulfanyl)-2-hydroxyimino-propionic acid ethyl ester, MS (ESI) m/z: 263 [M+H].

Example 6

3-p-Tolylsulfanyl-1-piperidin-1-propane-1,2-dione-2-oxime

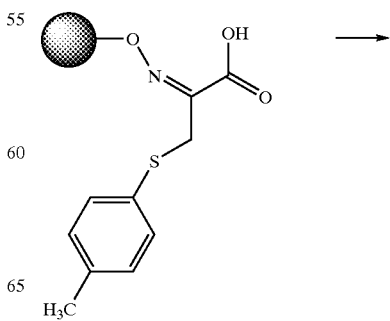

2-Hydroxyimino-3-piperidin-1-yl-thiopropionic Acid S-(2-Hydroxy-ethyl)ester

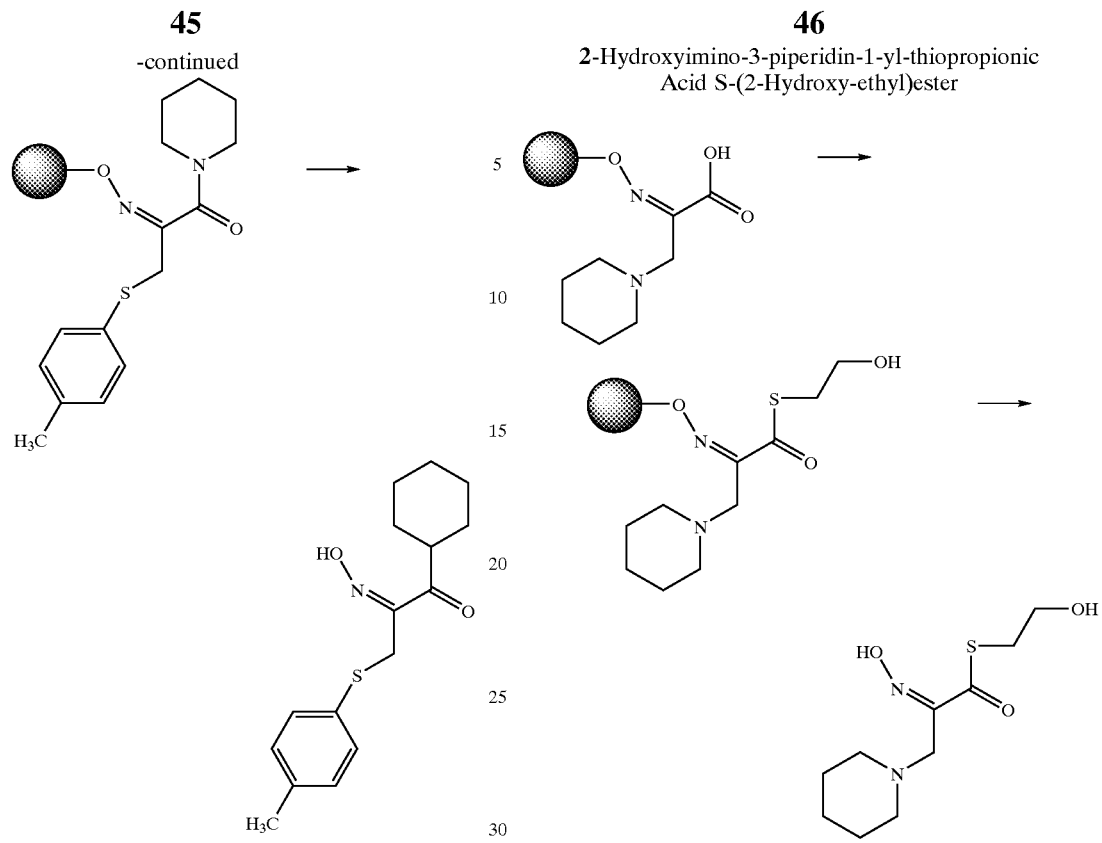

The pre-loaded Wang resin prepared as in Example 3(0.5 g, 0.665 mmol) was suspended in CH$_2$Cl$_2$ (20 mL) to which was added a solution of hydroxy benzotriazole (0.45 g, 3.325 mmol) in DMF (10 mL), followed by a solution of diisopropyl carbodiimide (0.42 g, 3.325 mmol) in CH$_2$Cl$_2$ (5 mL). The suspension was then agitated for 10 min. Piperidine (1.0 mL, large excess) was then added and the suspension agitated for 3 hrs. The resin was filtered, washed successively with DMF, CH$_2$Cl$_2$ and dried under vacuum to a constant weight to obtain resin-bound 1-piperidin-1-yl-3-p-tolylsulfanyl-propane-1,2-dione 2-oxime.

The resin was suspended in a mixture of TFA and CH$_2$Cl$_2$ (1:3, 25 mL total volume), agitated for 1 hr. The resin was filtered off, washed with CH$_2$Cl$_2$ (10 mL), and the combined organic filtrates were concentrated to yield 1-piperidin-1-yl-3-p-tolylsulfanyl-propane-1,2-dione 2-oxime as a brown oil which solidified on standing (160 mg), MS (ESI) m/z: 293 [M+H].

Similarly, following the procedure as described above, but replacing piperidine with the appropriate amine derivatives and utilizing, if needed, modifications known to those skilled in the art the following compounds were prepared:

2-Hydroxyimino-N-phenyl-3-p-tolylsulfanyl-propionamide;
3-(2-Diethylamino-ethylsulfanyl)-2-hydroxyimino-N-phenyl-propionamide, MS (ESI) m/z: 302 [M+H];
1,3-Di-piperidin-1-yl-propane-1,2-dione 2-oxime, MS (ESI) m/z: 254 [M+H] 3-Morpholin-4-yl-1-piperidin-1-yl-propane-1,2-dione 2-oxime, MS (ESI) m/z: 256 [M+H]; and
3-(4-Benzyl-piperazin-1-yl)-1-piperidin-1-yl-propane-1,2-dione 2-oxime MS (ESI) m/z: 345 [M+H]. Example 7

The pre-loaded Wang resin prepared as in Example 3 (0.5 g, 0.665 mmol) was suspended in CH$_2$Cl$_2$ (20 mL) to which was added a solution of hydroxy benzotriazole (0.45 g, 3.325 mmol) in DMF (10 mL), followed by a solution of diisopropyl carbodiimide (0.42 g, 3.325 mmol) in CH$_2$Cl$_2$ (5 mL). The suspension was then agitated for 10 min. 2-Mercaptoethanol(1.0 mL, large excess) was then added and the suspension agitated for 3 hrs. The resin was filtered, washed successively with DMF, CH$_2$Cl$_2$ and dried under vacuum to a constant weight to yield resin-bound 2-hydroxyimino-3-piperidin-1-yl-thiopropionic acid S-(2-hydroxy-ethyl)ester.

The resin was suspended in a mixture of TFA and CH$_2$Cl$_2$ (1:3, 25 mL total volume), agitated for 1 hr. The resin was filtered off, washed with CH$_2$Cl$_2$ (10 mL), and the combined organic filtrates were concentrated to yield 2-hydroxyimino-3-piperidin-1-yl-thiopropionic acid S-(2-hydroxy-ethyl) ester as a pale yellow oil (130 mg,), MS (ESI) m/z: 247 [M+H].

Similarly, following the procedure as described above, but replacing 2-mercaptoethanol with the appropriate thiol derivatives and utilizing, if needed, modifications known to those skilled in the art the following compounds were prepared:
2-Hydroxyimino-3-morpholin-4-yl-thiopropionic acid S-(2-hydroxy-ethyl)ester, MS (ESI) m/z: 249 [M+H], and
3-(4-Benzyl-piperazin-1-yl)-2-hydroxyimino-thiopropionic acid S-(2-hydroxy-ethyl)ester, MS (ESI) m/z: 338 [M+H].

What is claimed is:
1. A process for the synthesis of a pyruvate-derived compound, wherein the process comprises the steps of:
   forming an imine at the ketone position of a pyruvic acid substituted with a leaving group at carbon 3 with a solid-supported hydroxylamine to form a solid-supported intermediate;

performing a nucleophilic substitution of the solid-supported intermediate with a compound $R^2X(H)$;
wherein $R^2$ is an optionally substituted phenyl, heterocycle or heteroaryl,
where the heterocycle or heteroaryl contain, independently, one or more nitrogen, and/or oxygen, and/or sulfur atoms, and/or selenium;
where the one or more substituent on the phenyl, heterocycle or heteroaryl is independently substituted with one or more of hydroxy, alkyl, alkenyl, alkoxy, halo, nitro, sulphonate, —CN, amino, nitrile, carboxylate, ester, amide, phosphonate, and phosphate; or,
where $R^2$ is an optionally substituted alkyl or alkenyl group,
where the alkyl or alkenyl group is straight or branched chain, optionally substituted with one or more aryl, heteroaryl heterocyclyl, amino, hydroxy, halo, alkoxy, carbonyl, carboxylic acid, or amino acetyl; and
X is N, S; or
$R^2X$ is a tri-alkyl phosphite;
esterifying the solid-supported intermediate with a compound $R^1OH$ or $R^1SH$, or forming an amide with a compound $HNR^1R^{1a}$,
wherein $R^1$ is optionally substituted alkyl, alkenyl, cycloalkyl, aryl, alkoxy, ether, heteroaryl, heterocyclic, and alkoxyaryl,
wherein when $R^1$ comprises an alkyl or alkenyl group, the alkyl or alkenyl group is optionally substituted with one or more substituents selected from the group consisting of halo, hydroxy, esters and amides; or
when $R^1$ comprises a saturated or unsaturated ring, the saturated or unsaturated ring is optionally independently substituted with one or more substituents selected from the group consisting of alkyl, halo, nitro, amino, —CN, hydroxy, alkoxy, carboxylic acid, ester, and amide;
$R^{1a}$ is —H or $R^1$; and
cleaving the solid-supported intermediate from the solid support to yield a pyruvate-derived compound.

2. The process according to claim 1, further comprising the step of optionally splitting the solid-supported intermediate into multiple portions after any one of the steps.

3. The process according to claim 1, wherein said multiple portions are independently treated in the steps that follow the splitting.

4. The process according to claim 1, wherein the cleaving step is hydrolyzing the solid-supported intermediate from the solid support to yield a pyruvate analog.

5. The process according to claim 1, further comprising before the cleaving of the solid supported intermediate from the solid support the steps of:
reducing the solid-supported intermediate to an amine; and
of optionally acylating the solid-supported compound with a compound $R^3COL$ or alkylating with a compound $R^3CHO$ or $R^3CH_2L$ to form an O-linked solid-supported hydoxamate,
wherein L is a leaving group, and
—$R^3$ is a straight chain, branched chain or cyclic $C_1$–$C_{18}$ alkyl or $C_2$–$C_{18}$ alkenyl optionally substituted with heterocyclic, heteroaryl, aryl, halo, ester, amide;
optionally substituted aryl or heteroaryl, wherein the aryl or heteroaryl group may be independently substituted with one or more of —H, halo, straight chain or branched chain alkyl, lower alkyl, wherein lower alkyl is $C_1$–$C_6$, alkoxy, nitro, amino, —CN; or
optionally substituted heterocycle, independently substituted with one or more alkyl; carboxy; —$CF_3$; straight or branched chain alkyl, wherein the alkyl may be optionally independently substituted with one or more of —$CF_3$, amino, nitro, hydroxy, —CN, carboxy, or alkoxy.

6. The process according to claim 5, further comprising before the cleaving of the solid supported intermediate from the solid support the step of:
reducing the solid-supported intermediate to an amine.

7. The process according to claim 5, further comprising before the cleaving of the solid supported intermediate from the solid support the steps of:
reducing the solid-supported intermediate to an amine; and
of acylating the solid-supported compound with a compound $R^3COL$ to form an O-linked solid-supported hydoxamate,
wherein L is a leaving group, and
—$R^3$ is a straight chain, branched chain or cyclic $C_1$–$C_{18}$ alkyl or $C_2$–$C_{18}$ alkenyl optionally substituted with heterocyclic, heteroaryl, aryl, halo, ester, amide;
optionally substituted aryl or heteroaryl, wherein the aryl or heteroaryl group may be independently substituted with one or more of —H, halo, straight chain or branched chain alkyl, lower alkyl, wherein lower alkyl is $C_1$–$C_6$, alkoxy, nitro, amino, —CN; or
optionally substituted heterocycle, independently substituted with one or more alkyl; carboxy; —$CF_3$; straight or branched chain alkyl, wherein the alkyl may be optionally independently substituted with one or more of —$CF_3$, amino, nitro, hydroxy, —CN, carboxy, or alkoxy.

8. The process according to claim 5 further comprising before the cleaving of the solid supported intermediate from the solid support the steps of:
reducing the solid-supported intermediate to an amine; and
of alkylating with a compound $R^3CHO$ or $R^3COL$ to form an O-linked solid-supported hydoxamate,
wherein L is a leaving group, and
—$R^3$ is a straight chain, branched chain or cyclic $C_1$–$C_{18}$ alkyl or $C_2$–$C_{18}$ alkenyl optionally substituted with heterocyclic, heteroaryl, aryl, halo, ester, amide;
optionally substituted aryl or heteroaryl, wherein the aryl or heteroaryl group may be independently substituted with one or more of —H, halo, straight chain or branched chain alkyl, lower alkyl, wherein lower alkyl is $C_1$–$C_6$, alkoxy, nitro, amino, —CN; or
optionally substituted heterocycle, independently substituted with one or more alkyl; carboxy; —$CF_3$; straight chain or branched chain alkyl, wherein the alkyl may be optionally independently substituted with one or more of —$CF_3$, amino, nitro, hydroxy, —CN, carboxy, or alkoxy.

9. The process according to claim 4, further comprising the process of optionally splitting the solid-supported intermediate into multiple portions after any of the steps.

10. The process according to claim 9, wherein said multiple portions are independently treated in the steps that follow the splitting.

11. The process according to claim 1 wherein the step of esterification or amidation is done before the step of performing a nucleophilic substitution.

12. The process according to claim 5 wherein the step of esterification or amidation is done before the step of performing a nucleophilic substitution.

13. The process according to claim 1 further comprising the step of:
purifying the pyruvate derived compound.

14. The process according to claim 5 further comprising the step of:
purifying the pyruvate derived compound.

15. The process according to claim 1 wherein,
$R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;
$R^{1a}$ is hydrogen or $R^1$; or
$R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and
$R^2X$— is $R^2S$—, wherein $R^2$ is alkyl; cycloalkyl; aryl; heterocyclyl or heteroaryl, said heterocyclyl or heteroaryl including one or more heteroatoms independently selected from N, S, Se, and O, and all optionally substituted with one or more substituents selected independently from the group consisting of amino, alkyl, aryl, halo, nitro, hydroxy, —CN, and sulphonate.

16. The process according to claim 1 wherein
$R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;
$R^{1a}$ is hydrogen or $R^1$; or
$R^1R$ a together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and
$R^2X$— is $R^2N$—, wherein the N is within an 5- or 6-membered ring optionally incorporating one or two additional ring heteroatoms chosen from N, S, or O and optionally substituted with one or more substituents independently selected from the group consisting of amino, alkyl, alkoxy, aryl, halo, amide, nitro, —CN, carboxylic acid, ester, hydroxy, substituted amide, and sulphonate; or
$R^2X$ is —$NHR^d$ or —$NR^d_2$, wherein $R^d$ is independently selected from the group consisting of alkyl, aminoalkyl, alkenyl, arylalkyl, and hydroxyalkyl.

17. The process according to claim 1 wherein
$R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;
$R^{1a}$ is hydrogen or $R^1$; or
$R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl; and
$R^2X$ is a mono- or polyamino acid derivative.

18. The process according to claim 5 wherein,
$R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein said heteroatoms are selected from N, O and S;
$R^{1a}$ is hydrogen or $R^1$; or
$R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl;
$R^2X$— is $R^2S$—, wherein $R^2$ is alkyl; cycloalkyl; aryl; heterocyclyl or heteroaryl, said heterocyclyl or heteroaryl including one or more heteroatoms independently selected from N, S, Se, and O, and all optionally substituted with one or more substituents selected independently from the group consisting of amino, alkyl, aryl, halo, nitro, hydroxy, —CN, and sulphonate; and
$R^3$ is optionally substituted $C_1$–$C_{18}$ alkyl, optionally substituted $C_2$–$C_{18}$ alkenyl, optionally substituted aryl, optionally substituted heteroaryl or optionally substituted heterocyclyl.

19. The process according to claim 5 wherein,
$R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein the heteroatoms are selected from N, O and S;
$R^{1a}$ is hydrogen or $R^1$; or
$R^1 R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of =O, =S, straight chain or branched alkyl;
$R^2X$— is $R^2N$—, wherein the N is within an 5- or 6-membered ring optionally incorporating one or two additional ring heteroatoms chosen from N, S, or O and optionally substituted with one or more substituents independently selected from the group consisting of amino, alkyl, alkoxy, aryl, halo, amide, nitro, —CN, carboxylic acid, ester, hydroxy, substituted amide, and sulphonate; or
$R^2X$ is —$NHR^d$ or —$NR^d_2$, wherein $R^d$ is independently selected from the group consisting of alkyl, aminoalkyl, alkenyl, arylalkyl, and hydroxyalkyl, and
$R^3$ is optionally substituted $C_1$–$C_{18}$ alkyl, optionally substituted $C_2$–$C_{18}$ alkenyl, optionally substituted aryl, optionally substituted heteroaryl or optionally substituted heterocyclyl.

20. The process according to claim 5 wherein, $R^1$ is an optionally substituted group selected from the group consisting of $C_1$–$C_{18}$ alkyl; $C_2$–$C_{18}$ alkenyl; polyethyleneglycol; aryl; cycloalkyl; heterocyclyl and heteroaryl, wherein said heterocyclyl and heteroaryl include one or more heteroatoms and wherein the heteroatoms are selected from N, O and S;

$R^{1a}$ is hydrogen or $R^1$; or $R^1R^{1a}$ together with the nitrogen atom to which they are attached form a 5–7-membered ring, optionally incorporating one or two additional ring heteroatoms chosen from N, S or O, and said ring being optionally substituted with one or more substituents independently selected from the group consisting of $=O$, $=S$, straight chain or branched alkyl;

$R^2X$ is a mono- or poly-amino acid derivative, and $R^3$ is optionally substituted $C_1$–$C_{18}$ alkyl, optionally substituted $C_2$–$C_{18}$ alkenyl, optionally substituted aryl, optionally substituted heteroaryl or optionally substituted heterocyclyl.

21. The process of claim 1, wherein $R^2X$ is a tri-alkyl phosphite.

22. The process of claim 5, wherein $R^2X$ is a tri-alkyl phosphite.

* * * * *